United States Patent [19]
Lindig et al.

[11] Patent Number: 5,326,877
[45] Date of Patent: Jul. 5, 1994

[54] HERBICIDAL SUBSTITUTED TRIAZOLINONES

[75] Inventors: Markus Lindig, Kansas City, Mo.; Kurt Findeisen, Leverkusen, Fed. Rep. of Germany; Klaus-Helmut Müller, Duesseldorf, Fed. Rep. of Germany; Hans-Joachim Santel, Leverkusen, Fed. Rep. of Germany; Robert R. Schmidt, Bergisch-Gladbach, Fed. Rep. of Germany; Harry Strang, Kansas City, Mo.; Dieter Feucht, Monheim, Fed. Rep. of Germany; Klaus König, Odenthal, Fed. Rep. of Germany; Klaus Lürssen, Bergisch Gladbach, Fed. Rep. of Germany

[73] Assignee: Bayer Aktiengesellschaft, Leverkusen, Fed. Rep. of Germany

[21] Appl. No.: 962,442

[22] Filed: Oct. 16, 1992

Related U.S. Application Data

[60] Division of Ser. No. 660,321, Feb. 22, 1992, Pat. No. 5,194,085, which is a continuation-in-part of Ser. No. 433,650, Nov. 8, 1989, abandoned, which is a continuation-in-part of Ser. No. 409,175, Sep. 19, 1989, abandoned, which is a continuation-in-part of Ser. No. 200,995, May 31, 1988, abandoned.

[30] Foreign Application Priority Data

Jun. 12, 1987 [DE] Fed. Rep. of Germany ....... 3719575
Feb. 5, 1988 [DE] Fed. Rep. of Germany ....... 3803523
Nov. 19, 1988 [DE] Fed. Rep. of Germany ....... 3839206

[51] Int. Cl.$^5$ .................................. C07D 249/14
[52] U.S. Cl. ......................... 548/263.8; 548/263.4
[58] Field of Search ..................... 548/263.4, 263.8

[56] References Cited

PUBLICATIONS

Rudnicka et al, "Some Derivatives of 4-Amino, etc" CA 95: 203841j (1981).

Primary Examiner—Patricia L. Morris
Attorney, Agent, or Firm—Sprung Horn Kramer & Woods

[57] ABSTRACT

Herbicidally active substituted triazolinones of the formula

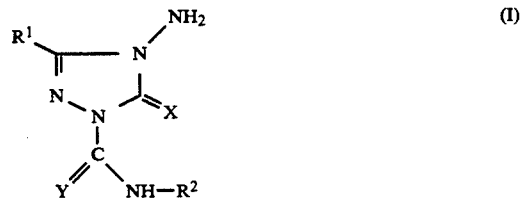

in which $R^1$ represents hydrogen, alkyl, alkenyl, alkinyl, halogenoalkyl, halogenoalkenyl, halogenoalkinyl, alkoxyalkyl, cycloalkyl, cycloalkylalkyl, or represents tetrahydrofuranyl, tetrahydrofuranylalkyl, or represents in each case optionally substituted aralkyl or aryl, $R^2$ represents hydrogen, alkyl, alkenyl, alkinyl, halogenoalkyl, halogenoalkenyl, halogenoalkinyl, cyanoalkyl, hydroxyalkyl, alkoxyalkyl, alkoxycarbonylalkyl, alkoxycarbonylalkenyl, alkylaminoalkyl, dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy, X represents oxygen or sulphur and
Y represents oxygen or sulphur.

New intermediates therefor are also shown.

16 Claims, No Drawings

HERBICIDAL SUBSTITUTED TRIAZOLINONES

This is a division of application Ser. No. 660,321, filed Feb. 22, 1992, now U.S. Pat. No. 5,194,085, which is a continuation-in-part of Ser. No. 07/433,650, filed Nov. 8, 1989, now abandoned, which is a continuation-in-part of Ser. No. 409,175, filed Sep. 19, 1989, now abandoned, which is a continuation-in-part of 200,995, filed May 31, 1988, now abandoned.

It is known that certain substituted triazolinones, such as, for example, the compound 4-amino-1-(N-isopropylcarbamoyl)-3-methylthio-(1H,4H)-1,2,4-triazolin-5-one or the compound 4-amino-1-(N-propylcarbamoyl)-3-methylthio-(1H,4H)-1,2,4-triazolin-5-one or the compound 4-amino-1-(N-butylcarbamoyl)-3-methylthio-(1H,4H)-1,2,4-triazolin-5-one or the compound 4-amino-1-(N-cyclohexylcarbamoyl)-3-methylthio-(1H,4H)-1,2,4-triazolin-5-one (cf., for example, JP 52/125,168), have herbicidal properties.

It has been disclosed that certain nitrogen heterocycles such as, for example, 4-amino-3-methyl-6-phenyl-1,2,4-triazin-5-one or N-isobutyl-2-oximidazolidine-1-carboxamide (compare, for example, DE-OS (German Published Specification) 2,364,474 and R. Wegler "Chemie der Pflanzenschutz- und Schädlingsbekämpfungsmittel, Vol. 5,219 (1977)) possess herbicidal properties.

However, the herbicidal activity of these previously known compounds with respect to problem weeds as well as their tolerability with respect to important cultivated plants is not completely satisfactory in all areas of application. Furthermore, certain substituted triazolinones, such as, for example, 1-(N,N-dimethylcarbonyl)-3-phenyl-4-amino-1,2,4-triazolin-5-one have been disclosed (compare J. Heterocycl. Chem. 17, 1691–1696 [1980]; Org. Mass. Spectrom. 14, 369–378 [1979]). Nothing has hitherto been disclosed about a herbicidal activity of these previously known triazolinones.

New substituted triazolinones of the general formula (I)

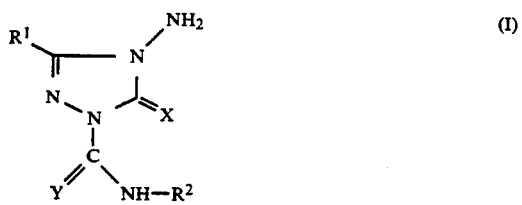

in which
$R^1$ represents hydrogen, alkyl, alkenyl, alkinyl, halogenoalkyl, halogenoalkenyl, halogenoalkinyl, alkoxyalkyl, cycloalkyl, cycloalkylalkyl, or represents tetrahydrofuranyl, tetrahydrofuranylalkyl, or represents in each case optionally substituted aralkyl or aryl,
$R^2$ represents hydrogen, alkyl, alkenyl, alkinyl, halogenoalkyl, halogenoalkenyl, halogenoalkinyl, cyanoalkyl, hydroxyalkyl, alkoxyalkyl, alkoxycarbonylalkyl, alkoxycarbonylalkenyl, alkylaminoalkyl, dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy,
X represents oxygen or sulphur and
Y represents oxygen or sulphur,
have been found.

The compounds of the formula (I) can optionally exist as geometric and/or optical isomers or isomer mixtures of different composition, depending on type of the substituents $R^1$ and $R^2$. Both the pure isomers and the isomer mixtures are claimed according to the invention.

Furthermore, it has been found that the new substituted triazolinones of the general formula (I)

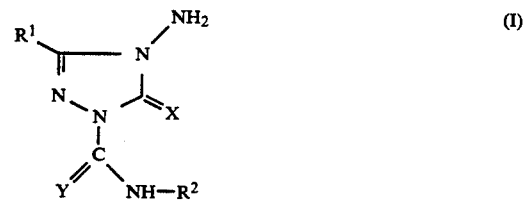

in which
$R^1$ represents hydrogen, alkyl, alkenyl, alkinyl, halogenoalkyl, halogenoalkenyl, halogenoalkinyl, alkoxyalkyl, cycloalkyl, cycloalkylalkyl, or represents tetrahydrofuranyl, tetrahydrofuranylalkyl, or represents in each case optionally substituted aralkyl or aryl,
$R^2$ represents hydrogen, alkyl, alkenyl, alkinyl, halogenoalkyl, halogenoalkenyl, halogenoalkinyl, cyanoalkyl, hydroxyalkyl, alkoxyalkyl, alkoxycarbonylalkyl, alkoxycarbonylalkenyl, alkylaminoalkyl, dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy,
X represents oxygen or sulphur and
Y represents oxygen or sulphur,
are obtained when
(a) hydrazones of the formula (II)

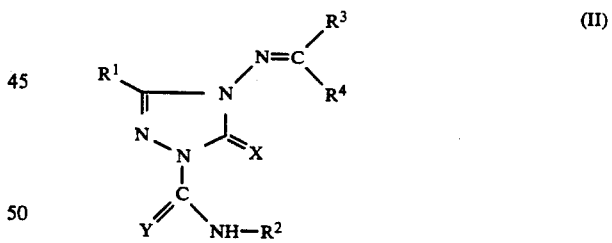

in which
$R^1$, $R^2$, X and Y have the abovementioned meaning and $R^3$ and $R^4$ independently of one another in each case represent hydrogen, alkyl, aralkyl or aryl,
are reacted with an acid, if appropriate in the presence of a diluent, or in that
b) 1H-triazolinones of the formula (III),

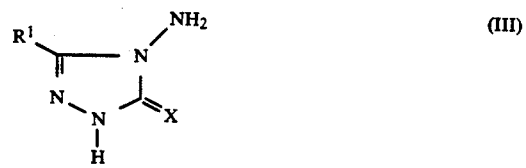

in which $R^1$ and X have the above mentioned meaning, are reacted with iso(thio)cyanates of the formula (IV),

  (IV)

in which
$R^2$ and Y have the above mentioned meaning,
if appropriate, in the presence of a diluent and, if appropriate, in the presence of a reaction auxiliary, or in that
c) triazolinones of the formula (V)

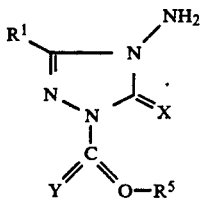  (V)

in which
$R^1$, X and Y have the above mentioned meaning and
$R^5$ represents alkyl, aryl or arylalkyl,
are reacted with amines of the formula (VI),

  (VI)

in which
$R^2$ has the above mentioned meaning,
if appropriate, in the presence of a diluent and, if appropriate, in the presence of a reaction auxiliary, or when
(d) 1H-triazolinones of the formula (III)

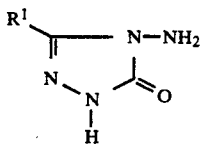  (III)

in which
$R^1$ has the abovementioned meaning,
are reacted with urethanes of the formula (VII)

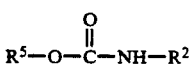  (VII)

in which
$R^2$ has the abovementioned meaning and
$R^5$ represents alkyl, aryl or arylalkyl,
if appropriate in the presence of a diluent and if appropriate in the presence of a reaction auxiliary.

Finally, it has been found that the new substituted triazolinones of the general formula (I) possess herbicidal properties.

Surprisingly, the substituted triazolinones of the general formula (I) according to the invention show a considerably higher herbicidal potency against problem weeds than the nitrogen heterocycles known from the prior art such as, for example, 4-amino-3-methyl-6-phenyl-1,2,4-triazin-5-one, 4-amino-1-(N-isopropylcarbamoyl)-3-methylthio-(1H,4H)-1,2,4-triazolin-5-one or the compound 4-amino-1-(N-propylcarbamoyl)-3-methylthio-(1H,4H)-1,2,4-triazolin-5-one or the compound 4-amino-1-(N-butylcarbamoyl)-3-methylthio-(1H,4H)-1,2,4-triazolin-5-one or the compound 4-amino-1-(N-cyclohexylcarbamoyl)-3-methylthio-(1H,4H)-1,2,4-triazolin-5-one, which are compounds of a similar chemical structure and a similar type of action.

Formula (I) provides a general definition of the substituted triazolinones according to the invention. Preferred compounds of the formula (I) are those in which
$R^1$ represents hydrogen, or represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl having 1 to 6 carbon atoms in the individual alkyl parts, or represents cycloalkyl or cycloalkylalkyl in each case having 3 to 7 carbon atoms in the cycloalkyl part and where appropriate 1 to 6 carbon atoms in the straight-chain or branched alkyl part, or represents tetrahydrofuranyl, or represents tetrahydrofuranylalkyl optionally having 1 to 4 carbon atoms in the straight-chain or branched alkyl part, or represents aralkyl or aryl in each case having 6 to 10 carbon atoms in the aryl part and where appropriate 1 to 6 carbon atoms in the straight-chain or branched alkyl part, and which are in each case optionally monosubstituted or polysubstituted by identical or different substituents; suitable aryl substituents in each case being: halogen, cyano, nitro and also in each case straight-chain or branched alkyl, alkoxy, alkylthio, halogenoalkyl, halogenoalkoxy or halogenoalkylthio in each case having 1 to 4 carbon atoms and where appropriate 1 to 9 identical or different halogen atoms,
$R^2$ represents hydrogen, or represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl in each case having 2 to 8 carbon atoms and 1 to 15 or 13 identical or different halogen atoms, cyanoalkyl having 1 to 8 carbon atoms, hydroxyalkyl having 1 to 8 carbon atoms and 1 to 6 hydroxyl groups, alkoxyalkyl, alkoxycarbonlalkyl or alkoxycarbonylalkenyl in each case having up to 6 carbon atoms in the individual alkyl or alkenyl parts, alkylaminoalkyl or dialkylaminoalkyl in each case having 1 to 6 carbon atoms in the individual alkyl parts, cycloalkyl having 12 carbon atoms or represents cycloalkyl, cycloalkylalkyl, cycloalkenyl or cycloalkenylalkyl in each case having 3 to 8 carbon atoms in the cycloalkyl or cycloalkenyl part and where appropriate 1 to 6 carbon atoms in the alkyl part, and which are in each case optionally monosubstituted or polysubstituted by identical or different substituents, suitable substituents in each case being: halogen, cyano and also in each case straight-chain or branched alkyl or halogenoalkyl in each case having 1 to 4 carbon atoms and where appropriate 1 to 9 identical or different halogen atoms or straight-chain or branched halogenalkenyl having up to 4 carbon atoms and 1 to 5 halogen atoms or in each case bivalent alkanediyl or alkenediyl in each case having up to 4 carbon atoms; furthermore, $R^2$ represents heterocyclylalkyl having 1 to 6 carbon atoms in the straight-chain or branched alkyl part and 1 to 9 carbon atoms and also 1 to 3 hetero atoms—in particular nitrogen, oxygen and/or sulphur—in the heterocyclic part, and which is optionally monosubstituted or polysubstituted in the heterocyclic part by identical or different substituents, suitable substituents being: halogen, cyano, nitro, and also in each case straight-chain or branched alkyl, alkoxy, alkylthio, halogenoalkyl, halogenoalkoxy, halogenoalkylthio or alkoxycarbonyl in each case having 1 to 5 carbon atoms and where appropriate 1 to 9 identical or different halogen atoms; furthermore, $R^2$ represents in each case straight-chain or branched alkoxy having 1 to 8 carbon atoms, alkenyloxy having 2 to 8 carbon atoms or alkinyloxy having 2 to 8 carbon atoms, or, finally, represents aralkyl, aroyl, aryl, aralkyloxy or aryloxy, in each case having 6 to 10 carbon atoms in the aryl part and where appropriate 1 to 8 carbon atoms in the straight-chain or branched alkyl part, and which are in each case optionally monosubstituted or polysubstituted by identical or different substituents, suitable alkyl substituents where appropriate being halogen and cyano and suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl in each case having 1 to 6 carbon atoms in the alkyl part and where appropriate 1 to 9 identical or different halogen atoms, cycloalkyl having 3 to 6 carbon atoms and phenoxy, or $R^2$ represents benzyl with a condensed—O—CH$_2$—O— group in the phenyl part, X represents oxygen or sulphur and Y represents oxygen or sulphur.

Particularly preferred compounds of the formula (I) are those in which $R^1$ represents hydrogen, methyl, ethyl, n- or i-propyl, n-, i-, s- or t-butyl, n- or i-pentyl, n- or i-hexyl, or represents allyl, propargyl, straight-chain or branched halogenoalkyl having 1 to 4 carbon atoms and 1 to 9 identical or different halogen atoms, in particular fluorine, chlorine or bromine, or represents methoxymethyl, ethoxymethyl, propoxymethyl, cyclopentyl, cyclohexyl, cyclopropyl, cyclopropylmethyl, cyclohexylmethyl, cyclohexylethyl, or represents tetrahydrofuranyl, or represents tetrahydrofuranylmethyl, or represents benzyl or phenyl, which are in each case optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^2$ represents hydrogen, methyl, ethyl, n- or i-propyl, n-, i-, s- or t-butyl, in each case straight-chain or branched pentyl, hexyl, heptyl, octyl, nonyl, decyl or dodecyl, or represents allyl, in each case straight-chain or branched butenyl, pentenyl or hexenyl, propargyl, in each case straight-chain or branched butinyl, pentinyl or hexinyl, or represents straight-chain or branched halogenoalkyl having 1 to 8 carbon atoms and 1 to 9 identical or different halogen atoms, in particular fluorine, chlorine or bromine, or represents in each case straight-chain or branched halogenoalkenyl or halogenoalkinyl having in each case 3 to 8 carbon atoms and 1 to 3 halogen atoms, in particular fluorine or chlorine, or represents in each case straight-chain or branched cyanoalkyl having 1 to 6 carbon atoms in the alkyl part, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl in each case having up to 4 carbon atoms in the individual alkyl or alkenyl parts, or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, which are in each case optionally monosubstituted, disubstituted or trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl, butadienediyl or dichloroallyl;

$R^2$ furthermore represents heterocyclylmethyl, heterocyclylpropyl or heterocyclylethyl, which are optionally monosubstituted, disubstituted or trisubstituted in the heterocyclic part by identical or different substituents, suitable heterocycles in each case being:

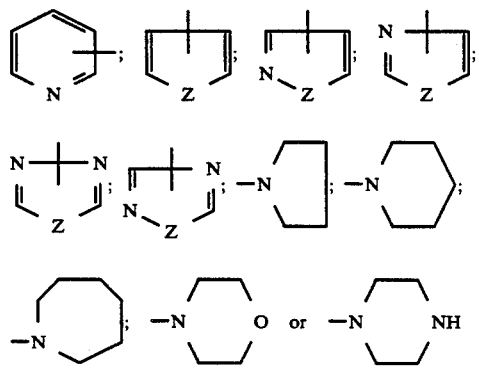

where

Z in each case represents oxygen or sulphur, and where suitable substituents in each case are: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio;

$R^2$ furthermore represents in each case straight-chain or branched alkoxy having 1 to 6 carbon atoms, alkenyloxy having 3 to 6 carbon atoms or alkinyloxy having 3 to 6 carbon atoms, or represents optionally straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, which are in each case optionally monosubstituted, disubstituted or trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, X represents oxygen or sulphur and Y represents oxygen or sulphur.

Very particularly preferred compounds of the formula (I) are those in which $R^1$ represents hydrogen, methyl, ethyl, n- or i-propyl, methoxymethyl, ethoxymethyl or propoxymethyl.

$R^2$ represents hydrogen, orrepresents methyl, ethyl, n- or i-propyl, n-, i-, s- or t-butyl, allyl, propargyl, in each case straight-chain or branched pentyl, hexyl, heptyl, octyl, butenyl, pentenyl, hexenyl, butinyl, pentinyl or hexinyl each of which is optionally monosubstituted, disubstituted or trisubstituted by halogen; or additionally represents cyclopropyl, cyclopentyl, cyclohexyl, cyclohexenyl, cyclopropylmethyl, cyclopropylethyl, cyclohexylmethyl, cyclohexylethyl or cycloheptyl which are in each case optionally monosubstituted, disubstituted or trisubstituted by identical or different substituents from the group comprising fluorine, chlorine, methyl, ethyl and/or cyano; and finally represents benzyl, phenylethyl or phenyl, X represents oxygen or sulphur and Y represents oxygen or sulphur.

Especially noteworthy are those compounds in which $R^1$ represents n-propyl, 1-propyl, n-butyl, i-butyl, s-butyl, t-butyl or cyclopropyl, or especially i-propyl, s-butyl or cyclopropyl, and X and Y represent oxygen.

The following substituted triazolinones of the general formula (I)

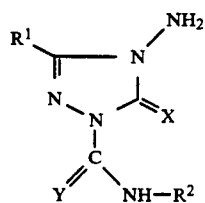

(I)

may be mentioned individually in addition to the compounds mentioned in the preparation examples:

| $R^1$ | $R^2$ | X | Y |
|---|---|---|---|
| CH₃ | 4-methylcyclohexyl | O | O |
| CH₃ | 2,2-difluoro-1-methylcyclopropyl | O | O |
| CH₃ | 3-methylcyclohex-3-enyl | O | O |
| CH₃ | —C(CH₃)₃ | O | S |
| CH₃ | —C(CH₃)₃ | S | S |
| CH₃ | cyclohexyl | S | S |
| CH₃ | 1-cyanocyclohexyl | O | O |
| C₂H₅ | —C(CH₃)₃ | O | O |
| C₂H₅ | —C(CH₃)₃ | O | S |
| C₂H₅ | —C(CH₃)₃ | S | O |
| C₂H₅ | cyclohexyl | O | S |
| C₂H₅ | cyclohexyl | S | O |
| C₂H₅ | phenyl | O | O |
| C₂H₅ | phenyl | O | S |
| C₂H₅ | benzyl | S | O |
| C₂H₅ | α-methylbenzyl (S-configuration) | O | O |
| H | —C(CH₃)₃ | O | O |
| H | cyclohexyl | O | O |
| H | phenyl | O | O |
| H | —C(CH₃)₃ | O | S |
| H | —C(CH₃)₃ | S | O |
| H | cyclohexyl | O | S |
| H | cyclohexyl | S | O |
| CH₃ | —C(CH₃)₂—CH₂—OCH₃ | O | O |
| CH₃ | —CH(CH₃)—CH(CH₃)₂ | O | O |
| CH₃ | —C(CH₃)₂—CH₂—N(CH₃)₂ | O | O |

-continued

| R¹ | R² | X | Y |
|---|---|---|---|
| CH₃ | -C(CH₃)₂-CH₂-N(piperidine) | O | O |
| CH₃ | -CH(CH₃)-CH(CH₃)-C₂H₅ | O | O |
| CH₃ | -CH(CH₃)-C₆H₃(OCH₃)₂ (3,4-dimethoxy) | O | O |
| CH₃ | -CH(CH₃)-C₆H₃(CH₃)₂ (3,4-dimethyl) | O | O |
| CH₃ | -CH(CH₃)-C₆H₄-C₂H₅ | O | O |
| CH₃ | -CH(CH₃)-C₆H₄-Br | O | O |
| CH₃ | -CH(CH₃)-C₆H₃Cl₂ (2,4-dichloro) | O | O |
| CH₃ | -CH₂-C(Cl)₂-C(CH₃)₂ (cyclopropane) | O | O |
| CH₃ | -C(CH₃)₂-CH(CH₃)₂ | O | O |
| CH₃ | -C(CH₃)₂-cyclopropyl | O | O |
| CH₃ | 2-chlorocyclohexyl (H) | O | O |
| CH₃ | -CH₂-CH₂-C₆H₄-CF₃ | O | O |
| CH₃ | -CH₂-CH₂-C₆H₄-Br | O | O |
| CH₃ | -CH₂-CH₂-C₆H₃(OCH₃)₂ (3,4-dimethoxy) | O | O |
| CH₃ | -CH(CH₃)-CH₂-C₆H₃(OCH₃)₂ (3,4-dimethoxy) | O | O |
| CH₃ | 2-methylcyclopropyl | O | O |
| CH₃ | 2,2-dichloro-1-methylcyclopropyl | O | O |
| CH₃ | 2,2-dichloro-3,3-dimethyl-1-methylcyclopropyl | O | O |
| CH₃ | 2,2-dichloro-1,3-dimethylcyclopropyl | O | O |
| CH₃ | 2,2-dichloro-3-methylcyclopropyl | O | O |
| CH₃ | -CH₂-C(CH₃)₂-C₆H₄-CH₃ | O | O |
| CH₃ | -C(CH₃)₂-cyclohexyl (H) | O | O |
| CH₃ | -C(CH₃)₂-cyclopentyl | O | O |
| CH₃ | -CH(CH₃)-cyclopentyl | O | O |
| CH₃ | -CH(C₂H₅)-(CH₂)₃-CH₃ | O | O |
| CH₃ | -CH(C₂H₅)-(CH₂)₂-CH₃ | O | O |
| CH₃ | -(CH₂)₃-CH(CH₃)₂ | O | O |

-continued

| R¹ | R² | X | Y |
|---|---|---|---|
| CH₃ | -CH(-CH(CH₃)₂)(-CH(CH₃)₂) (-CH with two -CH(CH₃)₂ groups) | O | O |
| CH₃ | -CH(CH₃)-CH₂-N(pyrrolidine) | O | O |
| CH₃ | -CH₂-CH(OCH₃)₂ | O | O |
| CH₃ | -CH(CH₃)-C(CH₃)₂-CN | O | O |
| CH₃ | -CH(CH₃)-CH₂-C(CH₃)₂-phenyl | O | O |
| CH₃ | -CH₂-(3,4-dihydro-2H-pyran-2-yl) | O | O |
| CH₃ | -C(CH₃)₃ | O | S |
| CH₃ | -*CH(CH₃)-phenyl  R-configuration | O | S |
| CH₃ | -*CH(CH₃)-phenyl  S-configuration | O | S |
| CH₃ | -CH(CH₃)-CH(CH₃)₂ | O | S |
| CH₃ | -CH(CH₃)-CH₂-OCH₃ | O | S |
| CH₃ | -(CH₂)₂-CH₃ | O | S |
| CH₃ | -CH(CH₃)₂ | O | S |
| CH₃ | -CH₂-CH(CH₃)₂ | O | S |

-continued

| R¹ | R² | X | Y |
|---|---|---|---|
| CH₃ | -CH(CH₃)-C₂H₅ | O | S |
| CH₃ | cyclopropyl | O | S |
| CH₃ | cyclopentyl | O | S |
| CH₃ | -(CH₂)₂-CH₃ | S | O |
| CH₃ | -(CH₂)₃-CH₃ | S | O |
| CH₃ | -CH₂-CH(CH₃)₂ | S | O |
| CH₃ | -CH(CH₃)-C₂H₅ | S | O |
| (CH₃)₂CH- | cyclohexyl (H) | O | O |
| (CH₃)₂CH- | cyclopentyl | O | O |
| (CH₃)₂CH- | -CH(cyclopropyl) | O | O |
| (CH₃)₂CH- | 1-methylcyclohexyl | O | O |
| (CH₃)₂CH- | 1-ethylcyclohexyl | O | O |
| (CH₃)₂CH- | 1-methylcyclopentyl | O | O |
| (CH₃)₂CH- | 1-ethylcyclopentyl | O | O |
| (CH₃)₂CH- | -CH₂-(4-Cl-phenyl) | O | O |
| (CH₃)₂CH- | -CH₂-CH₂-(4-Cl-phenyl) | O | O |
| (CH₃)₂CH- | -CH(CH₂F)₂ | O | O |

-continued

| R¹ | R² | X | Y |
|---|---|---|---|
| (CH₃)₂CH— | —C(CH₃)₂—CH=CH₂ | O | O |
| (CH₃)₂CH— | —C(CH₃)₂—CH₂—CH=CH₂ | O | O |
| (CH₃)₂CH— | —C(CH₃)₂—CH₂F | O | O |
| (CH₃)₂CH— | —C(CH₃)₂—CH₂Cl | O | O |
| (CH₃)₂CH— | —C(CH₂F)(CH₃)—CH₂F | O | O |
| (CH₃)₂CH— | —CH(CH₃)—CH₂—Cl | O | O |
| (CH₃)₂CH— | —C(CH₂Cl)(CH₃)—CH₂Cl | O | O |
| (CH₃)₂CH— | —C(CH₃)₂—CHCl₂ | O | O |
| (CH₃)₂CH— | —CH(CH₃)—CH₂—CH(CH₃)₂ | O | O |
| (CH₃)₂CH— | —CH(CH₃)—(CH₂)₂—CH(CH₃)₂ | O | O |
| (CH₃)₂CH— | —CH(CH₃)—(CH₂)₃—CH(CH₃)₂ | O | O |
| (CH₃)₂CH— | —C(CH₃)₂—CF₃ | O | O |
| (CH₃)₂CH— | —(CH₂)₂—CH₃ | O | O |
| (CH₃)₂CH— | —(CH₂)₃—CH₃ | O | O |
| (CH₃)₂CH— | —CH(CH₃)₂ | O | O |
| (CH₃)₂CH— | —CH(CH₃)—C₂H₅ | O | O |
| (CH₃)₂CH— | —CH(CH₃)—CH(CH₃)₂ | O | O |
| (CH₃)₂CH— | —CH(CH₃)—C₆H₅ | O | O |
| (CH₃)₂CH— | —CH(C₂H₅)—C₆H₅ | O | O |
| (CH₃)₂CH— | —CH(CH₃)₂—C₆H₅ | O | O |
| (CH₃)₂CH— | —C(CH₃)₂—C≡CH | O | O |
| (CH₃)₂CH— | —C(CH₃)(C₂H₅)—CH₃ | O | O |
| (CH₃)₂CH— | —C(CH₃)₂—(CH₂)₂—CH₃ | O | O |
| (CH₃)₂CH— | —C(CH₃)₂—(CH₂)₃—CH₃ | O | O |
| (CH₃)₂CH— | —C(CH₃)₃ | O | O |
| cyclopropyl-CH— | cyclohexyl-H | O | O |
| cyclopropyl-CH— | cyclopentyl | O | O |
| cyclopropyl-CH— | —CH(CH₂)(CH₂) (cyclopropyl) | O | O |
| cyclopropyl-CH— | 1-CH₃-cyclohexyl | O | O |
| cyclopropyl-CH— | 1-C₂H₅-cyclohexyl | O | O |
| cyclopropyl-CH— | 1-CH₃-cyclopentyl | O | O |
| cyclopropyl-CH— | 1-C₂H₅-cyclopentyl | O | O |

-continued

| R¹ | R² | X | Y |
|---|---|---|---|
| cyclopropyl (H₂C-CH-CH₂ ring) | -CH₂-C₆H₄-Cl (para) | O | O |
| cyclopropyl | -CH₂-CH₂-C₆H₄-Cl (para) | O | O |
| cyclopropyl | -CH(CH₂F)₂ | O | O |
| cyclopropyl | -C(CH₃)₂-CH=CH₂ | O | O |
| cyclopropyl | -C(CH₃)₂-CH₂-CH=CH₂ | O | O |
| cyclopropyl | -C(CH₃)₂-CH₂F | O | O |
| cyclopropyl | -C(CH₃)₂-CH₂Cl | O | O |
| cyclopropyl | -C(CH₃)(CH₂F)₂ | O | O |
| cyclopropyl | -CH(CH₃)-CH₂-Cl | O | O |
| cyclopropyl | -C(CH₂Cl)₂-CH₃ | O | O |
| cyclopropyl | -C(CH₃)₂-CHCl₂ | O | O |
| cyclopropyl | -CH(CH₃)-CH₂-CH(CH₃)₂ | O | O |
| cyclopropyl | -CH(CH₃)-(CH₂)₂-CH(CH₃)₂ | O | O |

-continued

| R¹ | R² | X | Y |
|---|---|---|---|
| cyclopropyl | -CH(CH₃)-(CH₂)₃-CH(CH₃)₂ | O | O |
| cyclopropyl | -C(CH₃)₂-CF₃ | O | O |
| cyclopropyl | -(CH₂)₂-CH₃ | O | O |
| cyclopropyl | -(CH₂)₃-CH₃ | O | O |
| cyclopropyl | -CH(CH₃)₂ | O | O |
| cyclopropyl | -CH(CH₃)-C₂H₅ | O | O |
| cyclopropyl | -CH(CH₃)-CH(CH₃)₂ | O | O |
| cyclopropyl | -CH(CH₃)-C₆H₅ | O | O |
| cyclopropyl | -CH(C₂H₅)-C₆H₅ | O | O |
| cyclopropyl | -C(CH₃)₂-C₆H₅ | O | O |
| cyclopropyl | -C(CH₃)₂-C≡CH | O | O |
| cyclopropyl | -C(CH₃)(C₂H₅)-CH₃ | O | O |
| cyclopropyl | -C(CH₃)₂-(CH₂)₂-CH₃ | O | O |

| R¹ | R² | X | Y |
|---|---|---|---|
| cyclopropyl-CH- (H₂C-CH(CH₂)-) | -C(CH₃)₂-(CH₂)₃-CH₃ | O | O |
| cyclopropyl-CH- | -C(CH₃)₃ | O | O |
| C₂H₅-CH(CH₃)- | cyclohexyl | O | O |
| C₂H₅-CH(CH₃)- | cyclopentyl | O | O |
| C₂H₅-CH(CH₃)- | -CH(CH₂)(CH₂) (cyclopropyl) | O | O |
| C₂H₅-CH(CH₃)- | 1-methylcyclohexyl | O | O |
| C₂H₅-CH(CH₃)- | 1-ethylcyclohexyl | O | O |
| C₂H₅-CH(CH₃)- | 1-methylcyclopentyl | O | O |
| C₂H₅-CH(CH₃)- | 1-ethylcyclopentyl | O | O |
| C₂H₅-CH(CH₃)- | -CH₂-C₆H₄-Cl (p) | O | O |
| C₂H₅-CH(CH₃)- | -CH₂-CH₂-C₆H₄-Cl (p) | O | O |
| C₂H₅-CH(CH₃)- | -CH(CH₂F)(CH₂F) (cyclopropyl-difluoro) | O | O |
| C₂H₅-CH(CH₃)- | -C(CH₃)₂-CH=CH₂ | O | O |
| C₂H₅-CH(CH₃)- | -C(CH₃)₂-CH₂-CH=CH₂ | O | O |
| C₂H₅-CH(CH₃)- | -C(CH₃)₂-CH₂F | O | O |
| C₂H₅-CH(CH₃)- | -C(CH₃)₂-CH₂Cl | O | O |
| C₂H₅-CH(CH₃)- | -C(CH₂F)₂-CH₃ | O | O |
| C₂H₅-CH(CH₃)- | -CH(CH₃)-CH₂-Cl | O | O |
| C₂H₅-CH(CH₃)- | -C(CH₂Cl)₂-CH₃ | O | O |
| C₂H₅-CH(CH₃)- | -C(CH₃)₂-CHCl₂ | O | O |
| C₂H₅-CH(CH₃)- | -CH(CH₃)-CH₂-CH(CH₃)₂ | O | O |
| C₂H₅-CH(CH₃)- | -CH(CH₃)-(CH₂)₂-CH(CH₃)₂ | O | O |
| C₂H₅-CH(CH₃)- | -CH(CH₃)-(CH₂)₃-CH(CH₃)₂ | O | O |
| C₂H₅-CH(CH₃)- | -C(CH₃)₂-CF₃ | O | O |
| C₂H₅-CH(CH₃)- | -(CH₂)₂-CH₃ | O | O |
| C₂H₅-CH(CH₃)- | -(CH₂)₃-CH₃ | O | O |
| C₂H₅-CH(CH₃)- | -CH(CH₃)₂ | O | O |
| C₂H₅-CH(CH₃)- | -CH(C₂H₅)(CH₃) | O | O |
| C₂H₅-CH(CH₃)- | -CH(CH₃)-CH(CH₃)₂ | O | O |
| C₂H₅-CH(CH₃)- | -CH(CH₃)-C₆H₅ | O | O |

-continued

| R¹ | R² | X | Y |
|---|---|---|---|
| C₂H₅—CH(CH₃)— | —CH(C₂H₅)—C₆H₅ | O | O |
| C₂H₅—CH(CH₃)— | —CH(CH₃)—CH(CH₃)—C₆H₅ | O | O |
| C₂H₅—CH(CH₃)— | —C(CH₃)₂—C≡CH | O | O |
| C₂H₅—CH(CH₃)— | —C(CH₃)(C₂H₅)—CH₃ | O | O |
| C₂H₅—CH(CH₃)— | —C(CH₃)₂—(CH₂)₂—CH₃ | O | O |
| C₂H₅—CH(CH₃)— | —C(CH₃)₂—(CH₂)₃—CH₃ | O | O |
| C₂H₅—CH(CH₃)— | —C(CH₃)₃ | O | O |

If, for example, 1-(N-isobutylcarbamoyl)-4-isopropylideneimino-3-methyl-1,2,4-triazolin-5-one is used as the starting compound, then the course of the reaction of the process (a) according to the invention can be represented by the following equation:

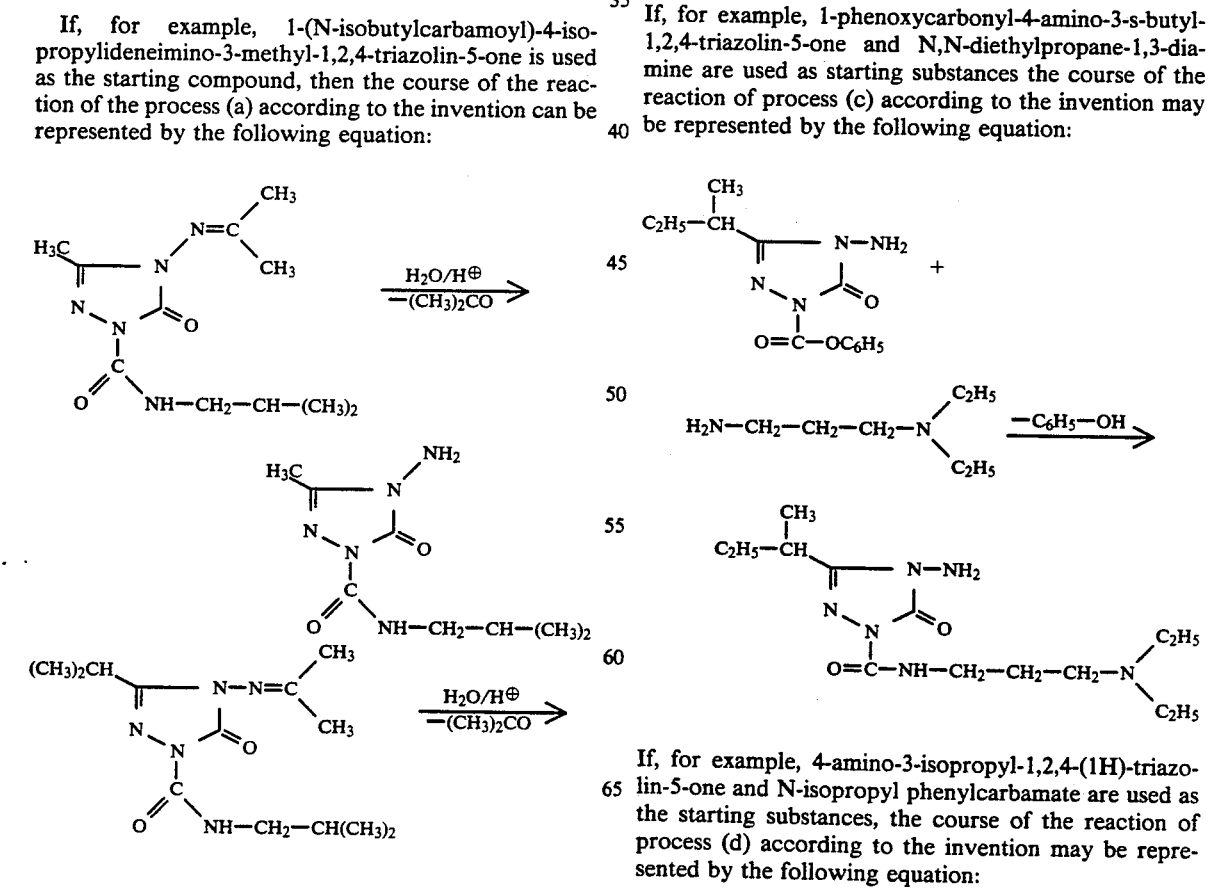

If, for example, 4-amino-3-cyclopropyl-1,2,4-(1H)-triazolin-5-one and t-butyl isocyanate are used as the starting substances, the course of the reaction of process (b) according to the invention may be represented by the following equation:

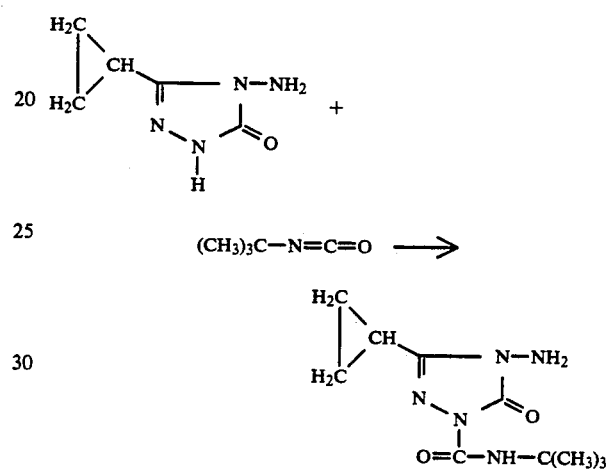

If, for example, 1-phenoxycarbonyl-4-amino-3-s-butyl-1,2,4-triazolin-5-one and N,N-diethylpropane-1,3-diamine are used as starting substances the course of the reaction of process (c) according to the invention may be represented by the following equation:

If, for example, 4-amino-3-isopropyl-1,2,4-(1H)-triazolin-5-one and N-isopropyl phenylcarbamate are used as the starting substances, the course of the reaction of process (d) according to the invention may be represented by the following equation:

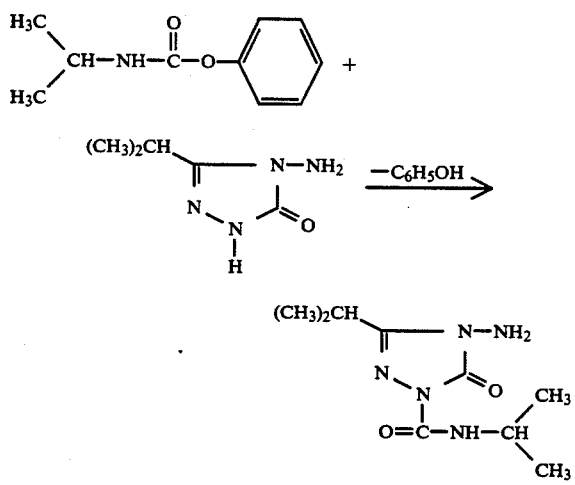

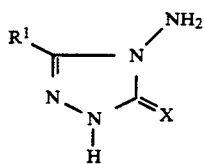

The hydrazones of the formula (II) were hitherto unknown. They are also subject matter of the present invention. However, they are obtained analogously to known processes (compare, for example, Acta Pol. Pharm. 38, 153-162 [1981] or C.A. 95: 203841j), for example when 1-unsubstituted 4-amino-triazolinones of the formula (III)

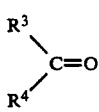 (III)

in which
R¹ and X have the abovementioned meaning,
are reacted with aldehydes or ketones of the formula (VII)

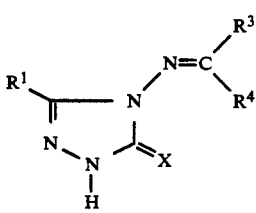 (VII)

in which
R³ and R⁴ have the abovementioned meaning,
if appropriate in the presence of a diluent such as, for example, dichloromethane or toluene, and if appropriate in the presence of a catalyst such as, for example, p-toluenesulphonic acid, at temperature between 40° C. and 120° C., and the 1-unsubstituted triazolinone-hydrazones of the formula (VIII)

(VIII)

in which
R¹, R³, R⁴ and X have the abovementioned meaning, thus obtainable are reacted in a subsequent 2nd step with iso(thio)cyanates of the formula (IV)

 (IV)

in which
R² and Y have the abovementioned meaning,
if appropriate in the presence of a diluent such as, for example, dichloromethane or dioxane, and if appropriate in the presence of a reaction auxiliary such as, for example, triethylamine, at temperatures between 50° C. and 150° C., or alternatively are reacted in a subsequent 2nd step with (thio)chloroformic acid esters of the formula

 (IX)

in which
R⁵ represents alkyl, aryl or arylalkyl and
Y has the abovementioned meaning,
if appropriate, in the presence of a diluent such as for example tetrahydrofuran and, if appropriate, in the presence of a reaction auxiliary such as for example sodium hydride or potassium-t-butylate at temperatures between −20° C. and +40° C. and the resulting triazolinones of the formula (X),

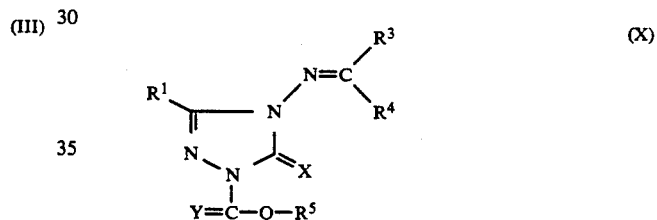 (X)

in which
R¹, R³, R⁴, R⁵, X and Y have the abovementioned meaning,
are reacted in a subsequent 3rd step with amines of the formula (VI),

 (VI)

in which
R² has the abovementioned meaning,
if appropriate, in the presence of a diluent such as for example tetrahydrofuran and, if appropriate, in the presence of a base, such as for example sodium hydroxide; potassium hydroxide or diazabicycloundecane (DBU), at temperatures between 20° C. and 50° C.

Some of the 1-unsubstituted 4-amino-triazolinones of the formula (III) are known and can be obtained in analogy to known processes (cf., for example, J. Heterocycl. Chem. 16, 403 [1979]; J. Heterocycl. Chem. 17, 1691 [1980]; Europ. J. Med. Chem. 18, 215 [1983]; Chem. Ber. 98, 3025 [1965]; Liebigs Ann. Chem. 637, 135 [1960]; J. Heterocycl. Chem. 21, 1769-1774 [1984]; chim. Acta Turc. 7, 269-290 [1979] or CA 106 (17): 138338e [1986]).

The aldehydes or ketones of the formula (VII) are generally known compounds of organic chemistry.

If, for example, 1-ethoxycarbonyl-4-amino-3-methyl-1,2,4-triazolin-5-one and N,N-diethylpropane-1,3-diamine are used as starting compounds, then the course of the reaction of the process (c) can be represented by the following equation:

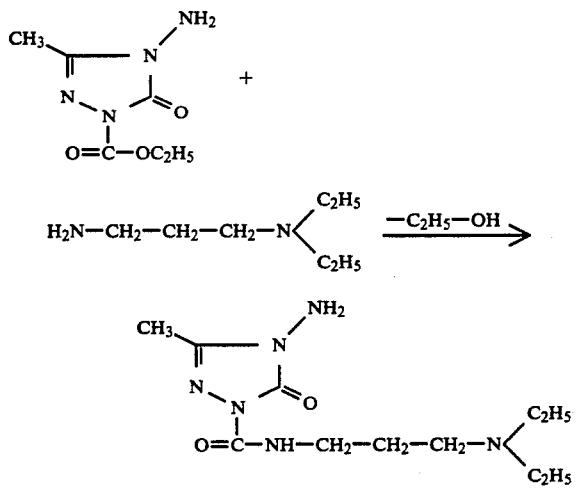

Formula (II) provides a general definition of the hydrazones required as starting materials for carrying out the process (a) according to the invention. In this formula (II), $R^1$, $R^2$, X and Y preferably represent those radicals which have already been mentioned as preferred for these substituents in connection with the description of the substances according to the invention, of the formula (I).

$R^3$ and $R^4$ in each case independently of one another preferably represent hydrogen, or represent straight-chain or branched alkyl having 1 to 4 carbon atoms, or represent pheyl or benzyl.

The majority of the 1-unsubstituted triazolinone hydrazones of the formula (VIII) are known (cf., for example, J. Heterocycl. Chem. 20, 77–80 [1983]; J. Heterocycl. Chem. 16, 403–407 [1979]; Chim. Acta. Turc. 7, 269–290 [1979]; J. chem. Soc.; Perkin Trans. II, 1973, 9–11; J. org. Chem. 36, 2190–2192 [1971]).

The (thio)chloroformic acid esters of the formula (IX) are generally known compounds of organic chemistry.

Some of the triazolinones of the formula (X) mentioned as intermediates are known (cf. for example Acta. Pol. Pharm. 38, 153–162 [1981] or C.A. 95: 203841j).

Triazolinones of the formula (Xa),

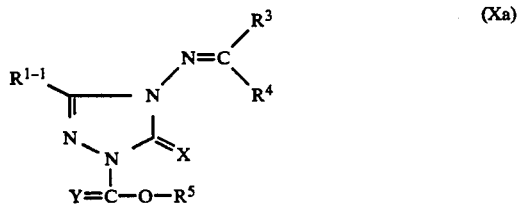

in which
$R^{1-1}$ represents alkyl and
$R^3$, $R^4$, $R^5$, X and Y have the abovementioned meaning, are not yet known and are also a subject of the present application.

$R^{1-1}$ preferably represents straight-chain or branched alkyl with 1 to 4, in particular with 1 to 3 carbon atoms; $R^{1-1}$ particularly preferably represents methyl, $R^3$ and $R^4$ preferably, in each case independently of one another represent hydrogen, straight-chain or branched alkyl with 1 to 4 carbon atoms or phenyl or benzyl, $R^5$ preferably represents straight-chain or branched alkyl with 1 to 4 carbon atoms for benzyl or phenyl, optionally mono- to trisubstituted by identical or different substituents, the following being possible substituents in each case; halogen, cyano, nitro, alkyl, alkoxy or alkylthio, each of which has 1 to 4 carbon atoms and each of which is straight-chain or branched, or halogenoalkyl, halogenoalkoxy or halogenoalkylthio, each of which has 1 to 4 carbon atoms and 1 to 9 identical or different halogen atoms and each of which is straight-chain or branched;

$R^5$ represents in particular methyl, ethyl, n- or i-propyl, n-, i-, s- or t-butyl, or benzyl or phenyl, optionally mono- to disubstituted by identical or different substituents, the following being possible substituents in each case: flourine, chlorine, bromine, cyano, nitro, methyl, ethyl, n-or i-propyl, n-, i-, s- or t-butyl, methoxy, ethoxy, n- or i-propoxy, methylthio, trifluoromethyl, trifluoromethoxy or trifluoromethylthio;

X and Y in each case independently of one another represent oxygen and sulphur, preferably oxygen.

The 1H-triazolinones required as starting materials for carrying out the process (b) according to the invention are defined generally by the formula (III). In this formula (III) $R^1$ and Z preferably represent those radicals which were already mentioned as preferred substituents in connection with the description of the compounds of the formula (I) according to the invention.

The 1H-triazolinones of the formula (III) are either known, or they can be obtained in analogy to known processes (cf., for example, B. J. Heterocycl. Chem. 16, 403 [1979]. J. Heterocycl. Chem. 17, 1691 [1980]; Europ. J. med. Chem. 18, 215 [1983]; Chem. Ber. 98, 3025 [1965]; Liebigs Ann. Chem. 637, 135 [1960]; J. Heterocycl. Chem. 21, 1769–1774 [1984]; Chim. Acta. Turc. 7, 269–270 [1979]; CA 106 (17): 138338e [1986]).

1-Unsubstituted 4-aminotriazolinones of the formula (IIIa)

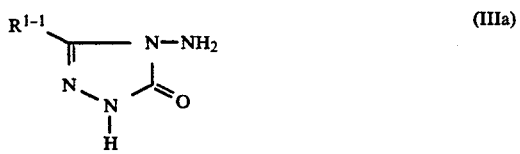 (IIIa)

in which
$R^{1-1}$ represents n-butyl, i-butyl, s-butyl or cyclopropyl, in particular represents s-butyl or cyclopropyl, were hitherto unknown and are also the subject-matter of the invention.

They are obtained in analogy to known processes (cf., for example, J. Heterocycl. Chem. 21, 1769 [1984], and Chem. Ber. 98, 3025 [1965]), for example when hydrazine hydrate is reacted with diphenyl carbonate in a customary manner, and the resulting carbonic acid hydrazide is cyclized, likewise in a customary manner, with carboxylic acid derivatives of the formula (XII)

$R^{1-1}$—COOR$^6$ (XII)

in which
$R^{1-1}$ has the abovementioned meaning and $R^6$ represents hydrogen, or represents straight-chain or branched alkyl having 1 to 4 carbon atoms, at temperatures between 150° C. and 250° C. (cf. also the preparation examples).

Carboxylic acid derivatives of the formula (XII) are generally known compounds of organic chemistry.

The iso(thio)cyanates also required as starting materials for carrying out the process (b) according to the invention are defined generally by the formula (IV). In this formula (IV) $R^2$ and Y preferably represent those radicals which have already been mentioned as preferred substituents in connection with the description of the compounds of the formula (I) according to the invention.

The iso(thio)cyanates of the formula (IV) are mostly known compounds of organic chemistry. The compounds 2,2,2-trifluoroisopropylcyanate and 2,2,2-trifluoro-1,1-dimethyl-ethylcyanate are not yet known but can however be prepared according to known methods. Iso(thio)cyanates can be obtained, for example, when corresponding amines are reacted with phosgene, if appropriate, in the presence of a base such as, for example, triethylamine (compare e.g. DE-OS2,804,802, DE-OS 2,512,514, U.S. Pat. Nos. 3,584,028, 2,706,753, 3,311,654, JA 50/29,599, Synthesis 1985, page 682 or J. Am. Chem. Soc. 77, 1901-1902 (1955)).

The triazolinones required as starting materials for carrying out the process (c) according to the invention are defined generally by the formula (V). In this formula (V), $R^1$, X and Y preferably represent those radicals which have already been mentioned as preferred substituents in connection with the description of the compounds of the formula (I) according to the invention.

$R^5$ preferably represent straight-chain or branched alkyl with 1 to 4 carbon atoms or benzyl or phenyl, optionally mono- to trisubstituted by identical or different substituents, the following being possible substituents in each case: halogen, cyano, nitro, alkyl, alkoxy or alkylthio, each of which has 1 to 4 carbon atoms and each of which is straight-chain or branched, or halogenoalkyl, halogenoalkoxy or halogenoalkylthio, each of which has 1 to 4 carbon atoms and 1 to 9 identical or different halogen atoms and each of which is straight-chain or branched;

$R^5$ represents in particular methyl, ethyl, n- or i-propyl, n-, i-, s- or t-butyl or benzyl or phenyl, optionally mono- to disubstituted by identical or different substituents, possible substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy or trifluoromethylthio.

Some of the triazolinones of the formula (V) are known (cf. for example J. Heterocycl. Chem. 17, 1691-1696 [1980]).

Triazolinones of the formula (Va)

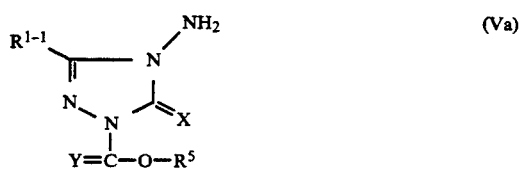

(Va)

in which $R^{1-1}$ represents alkyl, preferably straight-chain or branched alkyl with 1 to 4, in particular with 1 to 3 carbon atoms, and particularly preferably methyl and $R^5$, X and Y have the abovementioned meaning, are not yet known and are also a subject of the present application.

They are obtained analogously to the preparation of the known compounds of the formula (V), by reacting 1H-triazolinones of the formula (IIIa)

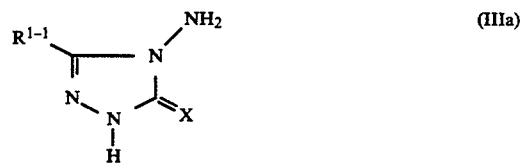

(IIIa)

in which $R^{1-1}$ and X have the abovementioned meaning, with (thio)chloroformic acid esters of the formula (IX),

(IX)

in which $R^5$ and Y have the abovementioned meaning, if appropriate in the presence of a diluent such as for example tetrahydrofuran and if appropriate in the presence of a reaction auxiliary such as for example potassium-t-butylate or sodium hydride at temperatures between $-20°$ C. and $+40°$ C. (cf. also the preparation examples).

The 1H-triazolinones of the formula (IIIa) are known or can be obtained analogously to known processes (cf. for example J. Heterocycl. Chem. 16, 403 [1979]; J. Heterocycl. Chem. 17, 1691 [1980]; Europ. J. med. Chem. 18, 215 [1983]; Chem. Ber. 98, 3025 [1965]; Liebigs Ann. Chem. 637, 135 [1960]).

Formula (VII) provides a general definition of the urethanes furthermore required as starting substances for carrying out process (d) according to the invention. In this formula (VII), $R^2$ preferably represents those radicals which have already been mentioned in connection with the description of the substances of the formula (I) according to the invention as being preferred for these substituents. $R^5$ preferably represents those radicals which have already been mentioned in connection with the description of the precursors of the formula (V) as being preferred, or particularly preferred, for this substituent.

The urethanes of the formula (VII) are generally known compounds of organic chemistry, or they can be obtained with the aid of generally known processes.

All inorganic and organic acids customarily utilizable for hydrazone cleavage are suitable as acids for carrying out the process (a) according to the invention. Inorganic mineral acids such as hydrochloric acid, sulphuric acid or phosphoric acid are preferably used.

All customary organic or inorganic solvents are suitable as diluents for carrying out the process (a) according to the invention. Polar organic solvents miscible with water, in particular alcohols, such as methanol, ethanol, propanol or butanol, their mixtures with water or pure water are preferably used as diluents.

The reaction temperatures can be varied within a relatively wide range in carrying out the process (a) according to the invention. In general, the reaction is carried out at temperatures between 20° C. and 150° C., preferably at temperatures between 50° C. and 120° C.

The process (a) according to the invention is customarily carried out at atmospheric pressure or under reduced pressure. If the process is carried out under reduced pressure, then suitable pressure ranges are between 20 and 400 mbar, preferably between 100 and 200 mbar.

For carrying out the process (a) according to the invention, 1 to 50 mols, preferably 1 to 20 mols, of acid are generally employed per mole of hydrazone of the formula (II). To achieve this, the hydrazone of the formula (II) is dissolved in a suitable amount of diluent, then the necessary amount of acid is added and the mixture is slowly concentrated under reduced pressure over several hours.

In a particular embodiment it is also possible to carry out the process (a) according to the invention and the preparation of the precursors of the formula (II) necessary for said process in one reaction step, in a so-called one-pot process.

For this purpose it is possible to select the triazolinones of the formula (X) as starting compounds and to react them successively, in a one-pot process, with amines of the formula (VI) and then with acid according to process (a) according to the invention (in this connection cf. also the preparation examples), or alternatively, to select the triazoline hydrazones of the formula (VIII) as starting compounds and to react them successively, in a one-pot process with (thio)chloroformic acid esters of the formula (IX), then with amines of the formula (VI) and then with acid according to process (a) according to the invention.

Inert organic solvents can be used as diluents for carrying out process (b) according to the invention. These include in particular aliphatic, alicyclic or aromatic, optionally halogenated hydrocarbons, such as for example benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethyl acetamide, N-methylformamide, N-methylpyrrolidone or hexamethylphosphoric acid triamide or esters, such as ethyl acetate.

The process (b) according to the invention is optionally carried out in the presence of a suitable reaction auxiliary. All customary inorganic or organic bases can be used as reaction auxiliaries. They include for example tertiary amines, such as triethylamine, N,N-dimethylaniline, N,N-diethylbenzylamine, N,N-dimethylcyclohexylamine or dibutyl tin dilaureate, pyridine, N,N-dimethylaminopyridine, diazabicyclooctane (DABCO), diazabicyclononene (DBN) and diazabicycloundecane (DBU).

When carrying out the process (b) according to the invention the reaction temperatures can be varied within a relatively large range. In general temperatures between 0° C. and 150° C., and preferably temperatures between 20° C. and 100° C. are used.

In general 1.0 to 2.0 mols, preferably 1.0 to 1.5 mols, of iso(thio)cyanate of the formula (IV) and, where appropriate, 0.001 to 2.0 mols, preferably 0.001 to 1.0 mol, of reaction auxiliaries are used per mol of 1H-triazolinone of the formula (III), for carrying out process (b) according to the invention.

The reaction, the working up and the isolation of the reaction products are carried out according to generally auxiliary methods.

Inert organic solvents can be used as diluents for carrying out the process (c) according to the invention. These include in particular aliphatic, alicyclic or aromatic, optionally halogenated hydrocarbons such as for example benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, nitriles, such as acetonitrile or propionitrile, amides, such as dimethyl formamide, dimethyl acetamide, N-methylformanilide, N-methylpyrrolidone or hexamethylphosphoric acid triamide or esters, such as ethyl acetate, or sulphoxides, such as dimethyl sulphoxide.

The processes (c) and (d) according to the invention can optionally be carried out in the presence of a suitable reaction auxiliary. All customary inorganic or organic bases are suitable as reaction auxiliaries. They include for example alkali metal hydroxides, such as sodium hydroxide or potassium hydroxide, alkali metal carbonates, such as sodium carbonate, potassium carbonate or sodium hydrogencarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecane (DBU).

When carrying out processes (C) and (d) according to the invention the reaction temperatures can be varied within a relatively large range. In general temperatures between 0° C. and 120° C. and preferably temperatures between 20° C. and 50° C. are used.

For carrying out process (c) according to the invention, 1.0 to 5.0 moles, preferably 1.0 to 2.5 moles, of amine of the formula (VI) and if appropriate 1.0 to 2.0 moles, preferably 1.0 to 1.2 moles, of reaction auxiliary are generally employed per mole of triazolinone of the formula (V). The reaction is carried out and the reaction products are worked up and isolated by generally customary methods.

In a special embodiment of the procedure, it is also possible to carry out process (c) according to the invention and to prepare the precursors of the formula (V) required for this, in one reaction step in a so-called one-pot process.

In this way of carrying out the reaction, the starting materials are 1H-triazolinones of the formula (III), which are reacted in succession in a one-pot process, initially with chloroformic acid esters of the formula (X) and subsequently with amines of the formula (VI), in accordance with process (c) according to the invention.

For carrying out process (d) according to the invention, 1.0 to 5.0 moles, preferably 1.0 to 2.5 moles, of urethane of the formula (VII) and, if appropriate, 1.0 to 5.0 moles, preferably 1.0 to 2.5 moles, of reaction auxiliary are generally employed per mole of 1H-triazolinone of the formula (III).

The reaction is carried out and the reaction products are worked up and isolated by generally customary methods.

Another method to obtain compounds of the formula (I) according to the invention comprises reacting oxadiazolinones of the formula (XI),

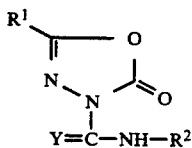

(XI)

in which
$R^1$, $R^2$ and Y have the abovementioned meaning,
with hydrazine hydrate in the presence of a suitable diluent such as for example methanol or ethanol at temperatures between 20° C. and 100° C. and thermally cyclizing the resulting carbazidic acid derivatives of the formula (XII).

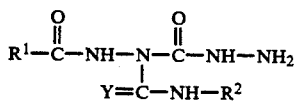

(XII)

in which
$R^1$, $R^2$ and Y have the abovementioned meaning,
in the presence of a suitable diluent such as for example toluene, chlorobenzene or dichlorobenzene, at temperatures between 80° C. and 200° C.

Oxadiazolinones of the formula (XI) are known (cf, for example FR 14 15 605 or C.A. 64: P5105 g and NL 6 510 645 or C.A. 65: P2274d-f) or can be obtained by generally known processes, for example by reacting the corresponding 4H-oxadiazolinones with iso(thio)cyanates of the formula (IV) by a procedure analogous to that used for carrying out the process (b) according to the invention or to that used for synthesizing the precursors of the formula (II).

The purification of the final products of the formula (I) is carried out with the aid of customary processes, for example by column chromatography or by recrystallization. The characterization is carried out with the aid of the melting point or with the aid of the proton nuclear magnetic resonance spectrum in the case of non-crystallizable compounds.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea and Mercurialis.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this way the active compounds according to the invention can be used with particularly good effect for combating monocotyledon and dicotyledon weeds, in particular in dicotyledon cultures, such as for example sugarbeets, corn, wheat and barley.

In particular, the outstanding activity against mercury (Mercurialis), a problem weed which is difficult to control, is worthy of mention.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic, meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. Other possible mixtures are those with 2,4-dichlorophenoxyacetic acid (2,4-D); 4-(2,4-dichlorophenoxy)butyric acid (2,4-DB); 2,4-dichlorophenoxypropionic acid (2,4-DP); N-(methoxymethyl)-2,6-diethyl-chloroacetanilide (ALACHLOR); 2-chloro-4-ethylamino-6-isopropylamino-1,3,5-triazine (ATRAZINE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); 3,6-dichloro-2-pyridinecarboxylic acid (CLOPYRALID); S-ethyl N,N-di-n-propyl-thiocarbamate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); 2-{[((4-methoxy-6-methyl-1,3,5-triazin-2-yl)-amino)carbonyl]-amino]-sulphonyl}-benzoic acid or its methyl ester (METSULFURON); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 2-chloro-N-isopropylacetanilide (PROPACHLOR); O-(6-chloro-3-phenyl-pyridazin-4-yl) S-octyl thiocarbonate (PYRIDATE); 2-chloro-4,6-bis-(ethylamino)-1,3,5-triazine (SIMAZINE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]thiophene-2-carboxylate (THIAMETURON); S-(2,3,3-trichloroallyl) N,N-diisopropylthiolcarbamate (TRI-ALLATE) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

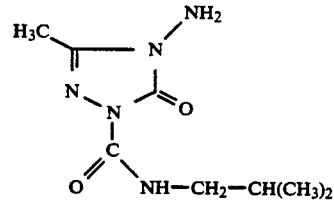

(process a)

20 ml of concentrated hydrochloric acid are added to 11.1 g (0.04 mol) of 1-(N-isobutylcarbamoyl)-4-isopropylideneimino-3-methyl-1,2,4-triazolin-5-one in 100 ml of ethanol and the solution is concentrated at 60° C. and about 200 mbar in the course of 5 hours on a rotary evaporator. The residue is brought to crystallization by trituration with ethanol/diethyl ether (1:1) and dried in air. 4.3 g (50% of theory) of 4-amino-1-(N-isobutylcarbamoyl)-3-methyl-triazolin-5-one of melting point 183° C. are obtained.

Example 2

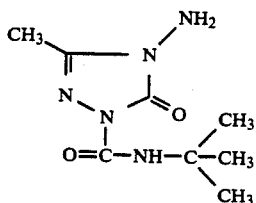

(process b)

3.6 g (0.036 mol) of t-butyl isocyanate and 0.05 g to 0.1 g of diazabicycloundecene (DBU) are added to 3.42 g (0.03 mol) of 4-amino-3-methyl-1,2,4-(1H)triazolin-5-one in 80 ml of absolute acetonitrile, the mixture is stirred for 2 hours at 20° C., concentrated in vacuo and the residue taken up in dichloromethane, the solution is washed with water, dried over sodium sulphate and concentrated in vacuo and the residue is crystallized by trituration with diethyl ether.

5.0 g (78.3% of theory) of 4-amino-1-(N-t-butylcarbamoyl)-3-methyl-1,2,4-triazolin-5-one of a melting point of 132° C. are obtained.

Example 3

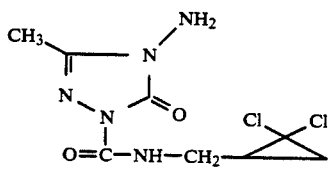

(process a - one-pot variant)

4.2 g (0.03 mol) of (2,2-dichlorocyclopropyl)methylamine are added to 8.2 g (0.03 mol) of 4-isopropylideneimino-3-methyl-1-phenoxycarbonyl-1,2,4-triazolin-5-one in 50 ml of absolute tetrahydrofuran, the mixture is then stirred for 12 hours at 20° C., concentrated in vacuo and the residue taken up in 100 ml of ethanol, 3 ml of concentrated hydrochlorid acid are added to the solution which is stirred for 3 to 4 hours at 60° C. and 200 mbar. For the working up the mixture is concentrated in vacuo, the residue is taken up in dichloromethane and the solution is washed three times with a saturated aqueous sodium hydrogen carbonate solution, dried over sodium sulphate and concentrated in vacuo. The residue is crystallized in vacuo. The residue is crystallized out by trituration with diethyl ether.

4.4 g (52% of theory) of 4-amino-1-[N-(2,2-dichlorocyclopropylmethyl)-carbamoyl]-3-methyl-1,2,4-triazolin-5-one of a melting point of 149° C. are obtained.

Example 4

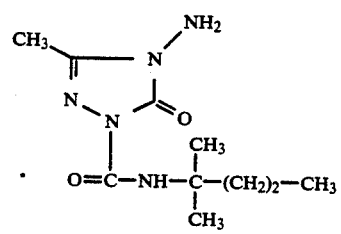

(process c)

8.9 g (0.088 mol) of 1,1-dimethylbutylamine are added to 3.2 g (0.0137 mol) of 4-amino-3-methyl-1-phenoxycarbonyl-1,2,4-triazolin-5-one in a mixture of 25 ml of tetrahydrofuran and 10 ml of dioxane, the mixture is heated to reflux temperature for 24 hours, concentrated in vacuo and the residue taken up in dichloromethane, the solution is washed with 2% sodium hydroxide solution and water, dried over sodium sulphate, the solvent removed in vacuo and the residue crystallized by trituration with diethyl ether.

1.9 g (61% of theory) of 4-amino-1-[N-(1,1-dimethylbutyl)-carbamoyl]-3-methyl-1,2,4-triazolin-5-one of a melting point of 110° C. are obtained.

The following substituted triazolinones of the general formula (I)

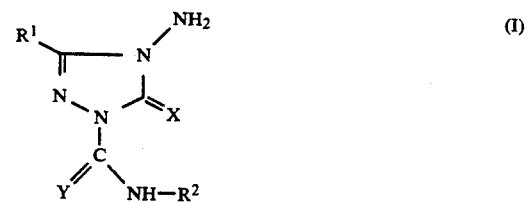

are obtained in a corresponding manner and according to the general instructions for the preparation:

TABLE 1

| Example No. | $R^1$ | $R^2$ | X | Y | physical properties |
|---|---|---|---|---|---|
| 5 | $CH_3$ | —CH(CH$_3$)—C$_6$H$_5$ (R) | O | O | $^1$H-NMR*) 1.5(d) |
| 6 | $CH_3$ | —CH(CH$_3$)—C$_6$H$_5$ (S) | O | O | $^1$H-NMR*) 1.5(d) |
| 7 | $C_2H_5$ | —C$_6$H$_{11}$ (H) | O | O | mp. 139° C. |

TABLE 1-continued

| Example No. | R¹ | R² | X | Y | physical properties |
|---|---|---|---|---|---|
| 8 | H | 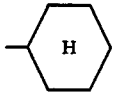 cyclohexyl (H) | O | O | mp. 161° C. |
| 9 | $CH_3$ | $-CH(CH_3)_2$ | O | O | mp. 63° C. |
| 10 | $CH_3$ | $-(CH_2)_5-CH_2Cl$ | O | O | $^1$H-NMR*) 1.45(m, 4H) |
| 11 | $CH_3$ | $-CH(CH_3)-C_2H_5$ | O | O | $^1$H-NMR*) 0.95(t, $CH_3$) |
| 12 | $CH_3$ | 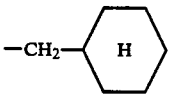 $-CH_2-$cyclohexyl(H) | O | O | mp. 133° C. |
| 13 | $CH_3$ | $-CH(C_2H_5)_2$ | O | O | mp. 103° C. |
| 14 | $CH_3$ | $-CH(CH_3)-CH(CH_3)_2$ | O | O | mp. 103° C. |
| 15 | $CH_3$ | 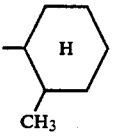 2-methylcyclohexyl | O | O | mp. 105° C. |
| 16 | $CH_3$ | 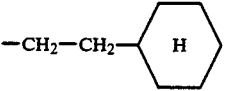 $-CH_2-CH_2-$cyclohexyl(H) | O | O | mp. 135° C. |
| 17 | $CH_3$ | $-CH_2-C(CH_3)_3$ | O | O | mp. 106° C. (decomp.) |
| 18 | $CH_3$ | 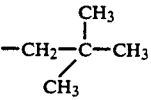 $-CH(CH_3)-(CH_2)_2-$phenyl | O | O | $n_D^{20}$ 1.5496 |
| 19 | $CH_3$ | 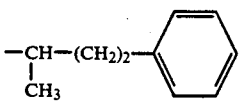 cyclohexyl(H) | S | O | mp. 128° C. |
| 20 | $CH_3$ | $-C(CH_3)_3$ | S | O | mp. 100° C. |
| 21 | H | $-(CH_2)_5-CH_2Cl$ | O | O | mp. 131° C. |
| 22 | $CH_3$ | 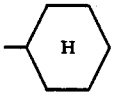 2,6-diethyl-4-methylcyclohexyl | O | O | mp. 153° C. |
| 23 | $CH_3$ | $-C(CH_3)_2-CH_2Cl$ | O | O | mp. 118° C. |

TABLE 1-continued

| Example No. | R¹ | R² | X | Y | physical properties |
|---|---|---|---|---|---|
| 24 | CH₃ | —CH₂—CH=CH₂ | O | O | mp. 92° C. |
| 25 | CH₃ | —CH₂—C(=O)—OC₂H₅ | O | O | mp. 127° C. |
| 26 | CH₃ | —C(CH₂Cl)(CH₃)(CH₂Cl) | O | O | $n_D^{22}$ 1.5055 |
| 27 | CH₃ | —C(CH₃)(CHCl₂)(CH₃) | O | O | mp. 176° C. |
| 28 | C₂H₅ | —CH₂—C(CH₃)(CH₃)(CH₃) | O | O | ¹H-NMR*): 4.4; 7.95 |
| 29 | CH₃ | —C(CH₂F)(CH₃)(CH₂F) | O | O | mp. 133° C. |
| 30 | C₂H₅ | —C(CH₂F)(CH₃)(CH₂F) | O | O | mp. 30–40° C. |
| 31 | CH₃ | —C(CH₃)(CH₃)(C₆H₅) | O | O | ¹H-NMR*): 4.36; 8.23 |
| 32 | CH₃ | —C(CH₃)(C₂H₅)(CH₃) | O | O | mp. 99° C. |
| 33 | CH₃ | —CH(CH₃)—(CH₂)₃—CH(CH₃)₂ | O | O | ¹H-NMR*): 4.40; 7.61 |
| 34 | CH₃ | cyclohexyl-CF₃ | O | O | mp. 162° C. |
| 35 | CH₃ | —CH₂—C₆H₅ | O | O | mp. 198° C. |
| 36 | CH₃ | —(CH₂)₃—CH₃ | O | O | mp. 108–109° C. |
| 37 | CH₃ | CH₃ | O | O | mp. 168–170° C. |
| 38 | CH₃ | —(CH₂)₂—CH₃ | O | O | mp. 134–136° C. |
| 39 | CH₃ | —CH(CH₃)—C(CH₃)(CH₃)—CH₃ | O | O | mp. 149° C. |
| 40 | CH₃ | —C(CH₃)(CF₃)(CH₃) | O | O | mp. 149–151° C. |

TABLE 1-continued

| Example No. | R¹ | R² | X | Y | physical properties |
|---|---|---|---|---|---|
| 41 | $CH_3$ | -cyclopentyl | O | O | mp. 93-94° C. |
| 42 | $CH_3$ | $-CH_2-CH_2-CN$ | O | O | mp. 175-178° C. |
| 43 | $CH_3$ | $-CH_2-CH(C_2H_5)-(CH_2)_3-CH_3$ | O | O | mp. 91-92° C. |
| 44 | $C_2H_5$ | $-C(CH_3)(CH_3)-C_2H_5$ | O | O | mp. 102-103° C. |
| 45 | $CH_3$ | $-C(CH_3)(CH_3)-CH_2-F$ | O | O | mp. 178° C. |
| 46 | $CH_3$ | 4-methylcyclohexyl (H) | O | O | mp. 113° C. |
| 47 | $CH_3$ | $-CH(C_2H_5)-C_6H_5$ | O | O | mp. 109° C. |
| 48 | $CH_3$ | cyclohexyl (H) | O | O | mp. 148° C. |
| 49 | $CH_3$ | $-CH(CH_3)-$cyclopropyl | O | O | ¹H-NMR*): 0.35-0.6; 0.93 |
| 50 | $CH_3$ | $-CH_2-C_6H_4-F$ (4-F) | O | O | mp. 175° C. |
| 51 | $CH_3$ | $-C(CH_3)(CH_3)-CH_2-N(morpholino)$ | O | O | mp. 211° C. (hydrochloride) |
| 52 | $CH_3$ | $-CH_2-C(CH_3)(CH_3)-C_6H_5$ | O | O | mp. 152° C. |
| 53 | $CH_3$ | $-C_2H_5$ | O | O | mp. 185° C. |
| 54 | $CH_3$ | $-CH_2-C(CH_3)(CH_3)-CH_2-N(CH_3)_2$ | O | O | mp. 198° C. (hydrochloride) |
| 55 | $CH_3$ | $-C(CH_3)(CH_3)-CH=C(Cl)(Cl)$ | O | O | mp. 135° C. |

TABLE 1-continued

| Example No. | R¹ | R² | X | Y | physical properties |
|---|---|---|---|---|---|
| 56 | $CH_3$ | -C₆H₄-C(CH₃)₃ (para) | O | O | mp. 200–203° C. |
| 57 | $CH_3$ | -C(CH₃)₂-C≡CH | O | O | mp. 119° C. |
| 58 | $CH_3$ | -CH(CH₃)-CH₂-Cl | O | O | mp. 136° C. |
| 59 | $CH_3$ | -C(CH₃)₂-CH₂-C(CH₃)₂-CH₃ | O | O | mp. 122° C. |
| 60 | $CH_3$ | -CH(CH₃)-CF₃ | O | O | mp. 141° C. |
| 61 | $CH_3$ | -C(CH₃)₂-CN | O | O | mp. 176° C. |
| 62 | $CH_3$ | -CH(CH₃)-(CH₂)₄-CH₃ | O | O | mp. 67° C. |
| 63 | $CH_3$ | -CH(CH₃)-CH₂-OCH₃ | O | O | mp. 120° C. |
| 64 | $CH_3$ | -(CH₂)₂-OCH₃ | O | O | mp. 114° C. |
| 65 | $CH_3$ | -CH(CH₃)-CH₂-N(C₂H₅)₂ | O | O | mp. 84° C. (hydrochloride) |
| 66 | $CH_3$ | -(CH₂)₃-CH₃ | O | S | mp. 147° C. |
| 67 | $CH_3$ | -CH₂-C₆H₅ | O | S | mp. 195° C. |
| 68 | $CH_3$ | -C₂H₅ | O | S | mp. 205° C. |
| 69 | $CH_3$ | -CH₃ | O | S | mp. 212° C. |
| 70 | $CH_3$ | -CH(CH₃)-(1-naphthyl) | O | O | mp. 139° C. |
| 71 | $CH_3$ | -CH(CH₃)-CH(CH₃)-Cl | O | O | mp. 114° C. |
| 72 | $CH_3$ | -CH(CH₃)-CH=CCl₂ | O | O | $n_D^{20}$ 1.5328 |

TABLE 1-continued

| Example No. | R¹ | R² | X | Y | physical properties |
|---|---|---|---|---|---|
| 73 | CH₃ | —CH(CH₂Cl)(CH=CH₂) | O | O | mp. 120° C. |
| 74 | CH₃ | —C(CH₃)₂—CH(CH₃)—CH=CCl₂ | O | O | $n_D^{20}$ 1.3840 |
| 75 | CH₃ | —CH(CH₂Cl)₂ and —CH₂—CHCl—CH₂Cl (3:1) | O | O | mp. 158° C. |
| 76 | CH₃ | —CH(C₂H₅)—CH₂Cl | O | O | mp. 147° C. |
| 77 | CH₃ | —CH(CH₃)—CH₂—N(morpholino) | O | O | $n_D^{22}$ 1.4995 (hydrochloride) |
| 78 | CH₃ | —C(CH₃)₂—(CH₂)₃—CH₃ | O | O | $n_D^{22}$ 1.4891 |
| 79 | —CH₃ | —CH(CH₃)—(CH₂)₅—CH₃ | O | O | $n_D^{20}$ 1.4920 |
| 80 | CH₃ | —CH(CH₃)—CH₂—C(CH₃)₃ | O | O | mp. 140° C. |
| 81 | CH₃ | —CH₂—CH(C₂H₅)₂ | O | O | mp. 115° C. |
| 82 | CH₃ | cyclopropyl | O | O | mp. 134° C. |
| 83 | CH₃ | 2,6-dimethylcyclohexyl | O | O | mp. 164° C. |
| 84 | CH₃ | 2,6-dimethylcyclohexyl (cis) | O | O | mp. 144° C. |
| 85 | CH₃ | 3,3,5-trimethylcyclohexyl | O | O | mp. 121° C. |

TABLE 1-continued

| Example No. | R¹ | R² | X | Y | physical properties |
|---|---|---|---|---|---|
| 86 | $CH_3$ | 2,6-diethylcyclohexyl (H) | O | O | ¹H-NMR*): 2.33 |
| 87 | $CH_3$ | $-CH_2-CF_3$ | O | O | mp. 152° C. |
| 88 | $CH_3$ | cyclohexyl (H) | O | S | mp. 178° C. |
| 89 | $CH_3$ | $-CH_2-$(2-Cl-phenyl) | O | O | mp. 156° C. |
| 90 | $CH_3$ | bicyclo[2.2.2]octyl | O | O | mp. 167° C. |
| 91 | $CH_3$ | $-CH_2-$bicyclo[2.2.2]octyl | O | O | mp. 113° C. |
| 92 | $CH_3$ | $-CH(CH_3)-$bicyclo[2.2.2]octyl | O | O | mp. 133° C. |
| 93 | $CH_3$ | $-CH(CH_2-CH(CH_3)_2)((CH_2)_2-phenyl)$ | O | O | mp. 98° C. |
| 94 | $CH_3$ | $-(CH_2)_2-$(2-$CH_3O$-phenyl) | O | O | mp. 156° C. |
| 95 | $CH_3$ | $-(CH_2)_2-$(4-$OCH_3$-phenyl) | O | O | mp. 210° C. |
| 96 | $CH_3$ | $-CH_2-$(3,4-methylenedioxyphenyl) | O | O | mp. 175° C. |
| 97 | $CH_3$ | $-CH_2-CH(CH_3)-C_2H_5$ | O | O | mp. 106° C. |
| 98 | $CH_3$ | $-(CH_2)_2-CH(CH_3)_2$ | O | O | mp. 104° C. |

TABLE 1-continued

| Example No. | R¹ | R² | X | Y | physical properties |
|---|---|---|---|---|---|
| 99 | CH₃ | 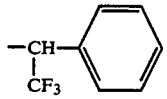 | O | O | mp. 120° C. (decomp.) |
| 100 | CH₃ | 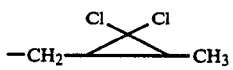 | O | O | mp. 108° C. |
| 101 | CH₃ | 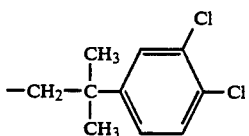 | O | O | mp. 151° C. |
| 102 | CH₃ | —(CH₂)₂—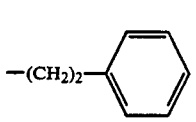 | O | O | mp. 151° C. |
| 103 | CH₃ | 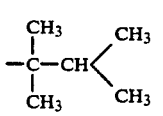 | O | O | mp. 134° C. |
| 104 | CH₃ | —CH(CH₃)—(CH₂)₂—CH₃ | O | O | $n_D^{20}$ 1.4972 |
| 105 | CH₃ | —C(C₂H₅)₃ | O | O | mp. 128° C. |
| 106 | CH₃ | 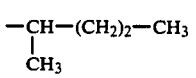 | O | O | mp. 101° C. |
| 107 | CH₃ | —CH(CH₃)—(CH₂)₂—CH(CH₃)₂ | O | O | mp. 73° C. |
| 108 | CH₃ | —(CH₂)₃—N(C₂H₅)₂ | O | O | $n_D^{20}$ 1.5815 (hydrochloride) |
| 109 | CH₃ | —(CH₂)₃—N(CH₃)₂ | O | O | mp. 210° C. (hydrochloride) |
| 110 | CH₃ | —CH(C₂H₅)—CH₂—CN | O | O | mp. 145° C. |
| 111 | CH₃ | —CH(C₂H₅)—CH₂—CH(CH₃)—C₂H₅ | O | O | $n_D^{20}$ 1.4890 |
| 112 | CH₃ | —CH(CH₃)—CH₂—CH(CH₃)₂ | O | O | $n_D^{20}$ 1.4858 |
| 113 | CH₃ | 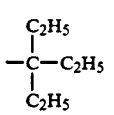 | O | O | mp. 108° C. (hydrochloride) |

TABLE 1-continued

| Example No. | R¹ | R² | X | Y | physical properties |
|---|---|---|---|---|---|
| 114 | $CH_3$ | $-(CH_2)_4-CH_3$ | O | O | mp. 81° C. |
| 115 | $CH_3$ | $-CH(CH_3)-(CH_2)_3-N(C_2H_5)_2$ | O | O | $n_D^{20}$ 1.5100 (hydrochloride) |
| 116 | $CH_3$ | $-CH(CH_3)-CH_2-N(CH_3)_2$ | O | O | $n_D^{20}$ 1.5150 (hydrochloride) |
| 117 | $CH_3$ | 1-methylcyclohexyl (H) | O | O | mp. 157° C. |
| 118 | $CH_3$ | 1-ethylcyclohexyl (H) | O | O | mp. 116° C. |
| 119 | $CH_3$ | 1-methylcyclopentyl | O | O | mp. 145° C. |
| 120 | $CH_3$ | 1-ethylcyclopentyl | O | O | mp. 118° C. |
| 121 | $CH_3$ | $-CH_2-CH_2-OC_2H_5$ | O | O | mp. 123° C. |
| 122 | $CH_3$ | phenyl | O | O | mp. 213° C. |
| 123 | $CH_3$ | 2,2-dimethyl-3-(2-methylpropenyl)cyclopropyl | O | O | mp. 93° C. |
| 124 | $CH_3$ | 2-methylcyclopropyl | O | O | mp. 93° C. |
| 125 | $CH_3$ | 2,2-dimethyl-3-(2,2-dichlorovinyl)cyclopropyl | O | O | 1H-NMR*): 1.58(dd); 1.77(t); 2.76(t) |
| 126 | $CH_3$ | cyclododecyl | O | O | mp. 142° C. |
| 127 | $CH_3$ | $-CH_2-$cyclohexyl | O | O | mp. 123° C. (endo-Form) |
| 128 | $CH_3$ | $-CH_2-$(1-methylcyclohexyl) | O | O | mp. 131° C. |

TABLE 1-continued

| Example No. | R¹ | R² | X | Y | physical properties |
|---|---|---|---|---|---|
| 129 | CH₃ | —CH(CH₃)—CH₂—C₆H₅ | O | O | mp. 133° C. |
| 130 | CH₃ | —CH₂-(2-furyl) | O | O | mp. 125° C. |
| 131 | CH₃ | —CH(CH₃)—C₆H₁₁ | O | O | mp. 117° C. |
| 132 | CH₃ | —C(CH₃)₂—CH₂—CH₂—C₆H₅ | O | O | ¹H-NMR*): 1.45(s); 7.04–7.43 (m) |
| 133 | CH3 | —CH₂—CH₂—C₆H₄—F | O | O | mp. 168° C. |
| 134 | CH₃ | —CH(C₂H₅)—C₆H₁₁ | O | O | mp. 118° C. |
| 135 | CH₃ | —CH(C₂H₅)—C(CH₃)₃ | O | O | mp. 157° C. |
| 136 | CH₃ | —CH₂—C(CH₃)₂—C₆H₄—Cl | O | O | mp. 180° C. |
| 137 | CH₃ | —CH₂—CH₂—C₆H₄—Cl | O | O | mp. 188° C. |
| 138 | CH₃ | —CH(CH₃)—C₆H₄—C₂H₅ | O | O | mp. 95° C. |
| 139 | C₂H₅ | —C(CH₃)₃ | O | O | m.p. 158° C. |
| 140 | C₂H₅ | —C(CH₃)₂—C≡CH | O | O | m.p. 119° C. |
| 141 | C₂H₅ | cyclopropyl | O | O | m.p. 106° C. |
| 142 | C₂H₅ | —CH(CH₃)₂ | O | O | m.p. 89° C. |
| 143 | C₂H₅ | —CH(CH₃)—CH₂Cl | O | O | $n_D^{22}$ 1.4929 |
| 144 | C₂H₅ | —CH(CH₃)—C₂H₅ | O | O | $n_D^{22}$ 1.4955 |

TABLE 1-continued
| Example No. | R¹ | R² | X | Y | physical properties |
|---|---|---|---|---|---|
| 145 | CH₃ | 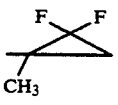 | O | O | m.p. 146° C. |
| 146 | C₂H₅ | 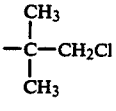 | O | O | m.p. 105° C. |
| 147 | CH₃ | —(CH₂)₁₁—CH₃ | O | O | m.p. 110° C. |
| 148 | CH₃ | —(CH₂)₁₅—CH₃ | O | O | m.p. 98° C. |
| 149 | CH₃ | —(CH₂)₁₇—CH₃ | O | O | m.p. 104° C. |
| 150 | CH₃ | 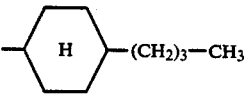 | O | O | m.p. 118° C. |
| 151 | CH₃ | 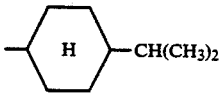 | O | O | m.p. 129° C. |
| 152 | CH₃ | 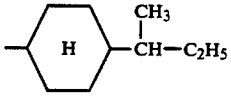 | O | O | m.p. 112° C. |
| 153 | CH₃ | 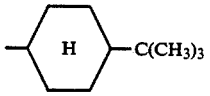 | O | O | m.p. 193° C. |
| 154 | CH₃ | 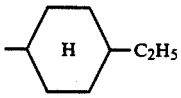 | O | O | m.p. 125° C. |
| 155 | C₂H₅ | 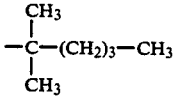 | O | O | $n_D^{20}$ 1.4896 |
| 156 | CH₃ | 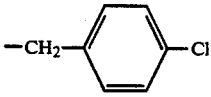 | O | O | m.p. 185° C. |
| 157 | CH₃ | 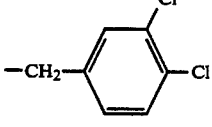 | O | O | m.p. 158° C. |
| 158 | CH₃ | 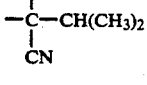 | O | O | m.p. 132° C. |
| 159 | CH₃ |  | O | O | m.p. 98° C. |
| 160 | CH₃ | 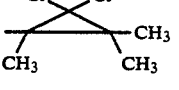 | O | O | m.p. 137° C. |

TABLE 1-continued

| Example No. | R¹ | R² | X | Y | physical properties |
|---|---|---|---|---|---|
| 161 | CH₃ | CH₃, Cl, Cl (cyclopropyl) | O | O | m.p. 162° C. |
| 162 | CH₃ | CH₃ (cyclopropyl) | O | O | m.p. 172° C. |
| 163 | C₂H₅ | cyclopentyl | O | O | m.p. 104° C. |

*)The ¹H-NMR spectra were recorded in deuterochloroform (CDCl₃) using tetramethylsilane (TMS) as the internal standard. The chemical shift is given as the δ-value in ppm.

EXAMPLE 164

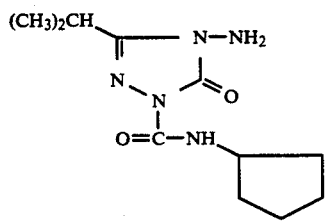

(Process (b))

6.1 g (0.055 mol) of cyclopentyl isocyanate and a small amount of diazabicycloundecene (DBU) are added to 7.1 g (0.05 mol) of 4-amino-3-isopropyl-(1H)-1,2,4-triazolin-5-one in 100 ml of absolute acetonitrile, the mixture is stirred for 12 hours at room temperature and then concentrated in vacuo, the residue is taken up in dichloromethane, the solution is washed with water to neutrality, dried over magnesium sulphate and concentrated, and the residue is crystallized by trituration with diethyl ether.

10.0 g (78% of theory) of 4-amino-1-(N-cyclopentyl-carbamoyl)-3-isopropyl-1,2,4-triazolin-5-one of melting point 109° C. are obtained.

Example 165

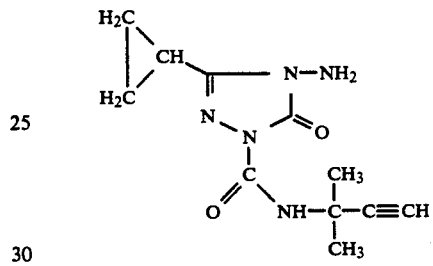

(Process (a) - one-pot variant)

5.5 g (0.05 mol) of 3-methyl-3-butinyl isocyanate and a small amount of diazabicycloundecene (DBU) are added to 11.1 g (0.05 mol) of 4-(4-methylpent-2-ylideneimino)-3-cyclopropyl-1,2,4-(1H)-triazolin-5-one in 150 ml of absolute acetonitrile, the mixture is stirred for 12 hours at 20° C. and subsequently concentrated in vacuo, the residue is taken up in aqueous ethanol, 2 ml of concentrated hydrochloric acid are added, the mixture is slowly concentrated at 60° C. under reduced pressure, the residue is taken up in dichloromethane, the solution is washed using saturated sodium hydrogen carbonate solution, dried over magnesium sulphate and concentrated, and the residue is crystallized by trituration with diethyl ether.

10.4 g (84% of theory) of 4-amino-3-cyclopropyl-1-[N-(3-methyl-3-butinyl)-carbamoyl]-1,2,4-triazolin-5-one of melting point 160° C. are obtained.

The following substituted triazolinones of the general formula (I) are obtained in a corresponding manner and following the general preparation instructions:

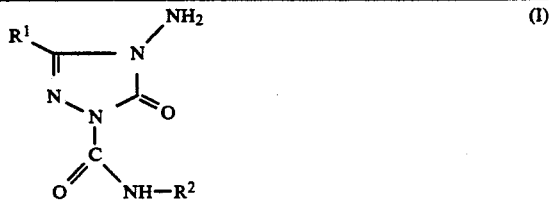

(I)

| Ex. No. | R¹ | R² | Physical constant |
|---|---|---|---|
| 166 | (CH₃)₃C— | —(CH₂)₅—CH₃ | $n_D^{20}$: 1.4980 |

-continued

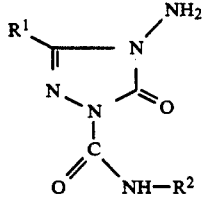

| Ex. No. | R¹ | R² | Physical constant |
|---|---|---|---|
| 167 | $CH_3-(CH_2)_2-$ | $-C(CH_3)_2-C\equiv CH$ | m.p 106° C. |
| 168 | $(CH_3)_2CH-$ | $-C(CH_3)_2-C\equiv CH$ | m.p. 90° C. |
| 169 | $(CH_3)_2CH-$ | -CH(cyclopropyl) | m.p. 133° C. |
| 170 | $CH_3-(CH_2)_2-$ | -CH(cyclopropyl) | m.p. 98° C. |
| 171 | $(CH_3)_3C-$ | -CH(cyclopropyl) | m.p. 158° C. |
| 172 | $CH_3-(CH_2)_2-$ | cyclohexyl | m.p. 100° C. |
| 173 | $(CH_3)_2CH-$ | cyclohexyl | $n_D^{20}$: 1.5168 |
| 174 | $CH_3-(CH_2)_2-$ | $-C(CH_3)_2-CH_2Cl$ | $n_D^{20}$: 1.5890 |
| 175 | $(CH_3)_2CH-$ | $-C(CH_3)_2-CH_2Cl$ | $n_D^{20}$: 1.5650 |
| 176 | $(CH_3)_3C-$ | cyclohexyl | ¹H-NMR*): 1,44(9H), 4,48(2H) |
| 177 | $(CH_3)_3C-$ | cyclopentyl | ¹H-NMR*): 1,44(9H), 4,53(2H) |
| 178 | $(CH_3)_3C-$ | $-C(CH_3)_3$ | m.p. 142° C. |
| 179 | $(CH_3)_3C-$ | 4-Cl-phenyl | m.p. 203° C. |

-continued $$(I)$$

Structure: R¹ group on a triazole ring with NH₂, N, N, C=O, and NH—R² substituents

| Ex. No. | R¹ | R² | Physical constant |
|---|---|---|---|
| 180 | CH₃—(CH₂)₂— | —C(CH₃)₃ | m.p. 112° C. |
| 181 | (CH₃)₂CH— | —C(CH₃)₃ | m.p. 108° C. |
| 182 | cyclopropyl (H₂C-CH-CH₂ ring) | —C(CH₃)₃ | m.p. 151° C. |
| 183 | (CH₃)₃C— | —*CH(CH₃)(C₆H₅), (S—) config. | $n_D^{20}$: 1.5171 |
| 184 | (CH₃)₃C— | —*CH(CH₃)(C₆H₅), (R+) config. | $n_D^{20}$: 1.5411 |
| 185 | (CH₃)₃C— | —C(CH₃)₂—CH₂—Cl | m.p. 133° C. |
| 186 | (CH₃)₃C— | —C(CH₃)₂—C≡CH | m.p. 148° C. |
| 187 | (CH₃)₃C— | —C(CH₃)₂—(CH₂)₃—CH₃ | $n_D^{20}$: 1.4844 |
| 188 | (CH₃)₃C— | —CH(CH₃)—CH(CH₃)₂ | m.p. 135° C. |
| 189 | (CH₃)₃C— | —C(CH₃)₂—CH₂F | m.p. 141° C. |
| 190 | (CH₃)₃C— | —CH₂—C₆H₄—Cl (4-Cl) | m.p. 208° C. |
| 191 | (CH₃)₃C— | —C(CH₃)₂—C₆H₅ | $n_D^{20}$: 1.5520 |
| 192 | (CH₃)₃C— | —(CH₂)₂—C₆H₄—Cl (4-Cl) | m.p. 172° C. |

-continued

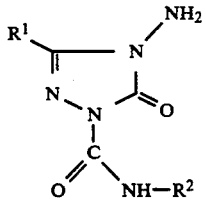

| Ex. No. | R¹ | R² | Physical constant |
|---|---|---|---|
| 193 | $(CH_3)_2CH-$ | $-CH(CH_3)-C_2H_5$ | m.p. 83° C. |
| 194 | $(CH_3)_2CH-$ | $-C(CH_3)_2-C_2H_5$ | $n_D^{20}$: 1,4801 |
| 195 | cyclopropyl-CH- | cyclohexyl-H | m.p. 177° C. |
| 196 | cyclopropyl-CH- | cyclopentyl- | m.p. 107° C. |
| 197 | $(CH_3)_2CH-$ | $-C(CH_3)_2-CH_2F$ | m.p. 124° C. |
| 198 | $(CH_3)_2CH-$ | $-C(CH_3)(CH_2Cl)_2$ | $^1$H-NMR*): 1,34(6H), 3,12(1H), 4,40(2H) |
| 199 | $(CH_3)_2CH-$ | $-C(CH_3)_2-CHCl_2$ | m.p. 121° C. |
| 200 | $(CH_3)_2CH-$ | $-CH(CH_3)_2$ | m.p. 124° C. |
| 201 | $(CH_3)_2CH-$ | $-C(CH_3)_2-(CH_2)_3-CH_3$ | $n_D^{20}$: 1,4874 |
| 202 | $(CH_3)_2CH-$ | $-C(CH_3)_2-(CH_2)_3-CH_3$ | $n_D^{20}$: 1,4847 |
| 203 | $(CH_3)_2CH-$ | $-CH(CH_3)-CH(CH_3)_2$ | $n_D^{20}$: 1.4860 |
| 204 | $(CH_3)_2CH-$ | $-\overset{*}{C}H(CH_3)-C_6H_5$ (S−) config. | $n_D^{20}$: 1.5308 |
| 205 | $(CH_3)_2CH-$ | $-C(CH_3)_2-C_6H_5$ | $n_D^{20}$: 1.5355 |

-continued

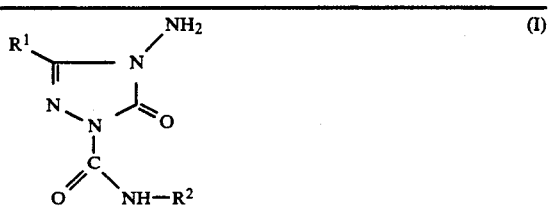

| Ex. No. | R¹ | R² | Physical constant |
|---|---|---|---|
| 206 | $(CH_3)_2CH-$ | H₃C-[1-methylcyclopentyl] | $n_D^{20}$: 1.5011 |
| 207 | cyclopropyl-CH- | $-C(CH_3)_2-CH_2Cl$ | m.p. 94° C. |
| 208 | cyclopropyl-CH- | $-C(CH_3)_2-CH_2F$ | m.p. 138° C. |
| 209 | $(CH_3)_2CH-$ | 2-chlorocyclohexyl | amorphous<br>δ = 1.34 Duplett (2CH₃)<br>3.13 Multiplett (1H)<br>3.90 Multiplett (2H)<br>4.48 Singulett (NH₂)<br>8.04 Duplett (NH) |
| 210 | cyclopropyl-CH- | 2-chlorocyclohexyl | amorphous<br>δ = 1.05 Multiplett (2H, cyclopropyl)<br>1.16 Multiplett (2H, cyclopropyl)<br>2.06 Multiplett (1H, cyclopropyl)<br>3.89 Multiplett (2H)<br>4.55 Singulett (NH₂)<br>8.03 Duplett (NH) |
| 211 | $(CH_3)_2CH$ | $-C_4H_9-n$ | $n_D^{20}$: 1,4969 |
| 212 | cyclopropyl-CH- | $-C_4H_9-n$ | mp: 84° C. |

*)The ¹H-NMR spectra were recorded in deuterochloroform (CDCl₃) with tetramethylsilane (TMS) as the internal standard. The chemical shift is indicated as a δ value in ppm.

Preparation of the starting compounds

Example II-1

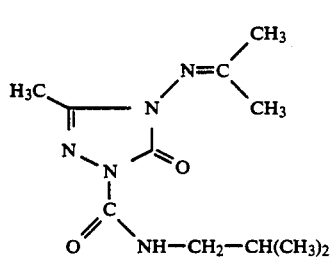

12 g (0.12 mol) of isobutyl isocyanate are added dropwise at 20° C. with stirring to 6 g (0.04 mol) of 4-isopropylideneimino-3-methyl-1H-triazolin-5-one and 4 g (0.04 mol) of triethylamine in 20 ml of dioxane and the mixture is stirred for 3 hours at 100° C. after completion of the addition. For working up, the reaction mixture is concentrated in vacuo, the residue is taken up in 100 ml of dichloromethane, and the solution is washed repeatedly with 100 ml of water in each case, dried over sodium sulphate and freed from solvent in vacuo.

11.2 g (100% of theory) of 1-(N-isobutylcarbamoyl)-4-isopropylideneimino-3-methyl-1,2,4-triazolin-5-one are obtained as an oil.

¹H-NMR (CDCl₃): δ=0.85 (d, 6H) ppm.

The following initial products of the general formula (II)

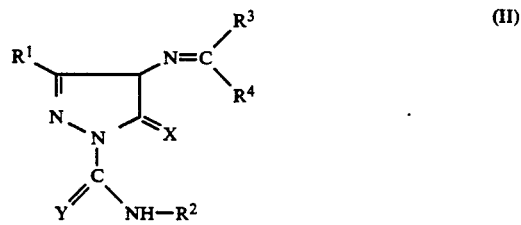

are obtained in a corresponding manner and according to the general instructions for the preparation:

TABLE 2

$$=C\begin{matrix}R^3\\R^4\end{matrix}$$

| Example No: | R¹ | R² | =C(R³)(R⁴) | X | Y | physical properties |
|---|---|---|---|---|---|---|
| II-2 | CH₃ | cyclohexyl-H | =C(CH₃)₂ | O | O | mp. 125° C. |
| II-3 | CH₃ | cyclohexyl-H | =CH—CH(CH₃)₂ | O | O | ¹H-NMR*) 3.9 |
| II-4 | CH₃ | —CH(CH₃)—C₂H₅ | =C(CH₃)₂ | O | O | mp. 87° C. |
| II-5 | CH₃ | —CH(CH₃)₂ | =C(CH₃)₂ | O | O | mp. 107° C. |
| II-6 | CH₃ | —CH(C₂H₅)₂ | =C(CH₃)₂ | O | O | mp. 68° C. |
| II-7 | CH₃ | —CH—CH(CH₃)₂ | =C(CH₃)₂ | O | O | ¹H-NMR*) 0.54(d, CH₃) |
| II-8 | CH₃ | —CH₂—cyclohexyl-H | =C(CH₃)₂ | O | O | mp. 115° C. |
| II-9 | CH₃ | —C(CH₃)₂—CH₂Cl | =C(CH₃)₂ | O | O | mp. 88° C. |
| II-10 | CH₃ | 2-methylcyclohexyl | =C(CH₃)₂ | O | O | mp. 139° C. |
| II-11 | CH₃ | 2,6-diethyl-4-methylcyclohexyl | =C(CH₃)₂ | O | O | oil |
| II-12 | CH₃ | —CH₂—COOC₂H₅ | =C(CH₃)₂ | O | O | mp. 108° C. |
| II-13 | CH₃ | —CH₂—CH=CH₂ | =C(CH₃)₂ | O | O | mp. 86° C. |
| II-14 | CH₃ | 3-CF₃-phenyl | =C(CH₃)₂ | O | O | mp. 158° C. |
| II-15 | CH₃ | 4-OCF₃-phenyl | =C(CH₃)₂ | O | O | mp. 218° C. |
| II-16 | CH₃ | 3-CF₃-4-Cl-phenyl | =C(CH₃)₂ | O | O | mp. 185° C. |

TABLE 2-continued

| Example No: | R¹ | R² | =C<R³/R⁴ | X | Y | melting point (°C.) |
|---|---|---|---|---|---|---|
| II-17 | CH₃ | —CH₂—C(CH₃)(CH₃)—CH₃ | =C(CH₃)₂ | O | O | mp. 121–122° C. |
| II-18 | CH₃ | —C(CH₃)(CH₂Cl)—CH₃ | =CH—(3-OCF₃-C₆H₄) | O | O | 80 |
| II-19 | CH₃ | —C(CH₃)(CH₂Cl)—CH₃ | =CH—(3-CF₃-C₆H₄) | O | O | 137 |
| II-20 | CH₃ | —C(CH₃)(CH₂Cl)—CH₃ | =CH—(3-Cl-C₆H₄) | O | O | 163 |
| II-21 | CH₃ | —C(CH₃)(C₂H₅)—CH₃ | =CH—CH(CH₃)—CH₂—CH(CH₃)₃ | O | O | 77 |

Example III-1

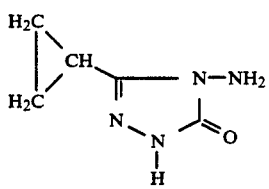

1892 g (8.84 mol) of diphenyl carbonate are added in portions to 884 g (17.68 mol) of hydrazine hydrate with stirring and ice-cooling, so that the temperature of the reaction mixture does not exceed 30° C. When the addition is complete, the mixture is stirred for about 3 hours at 80° C., any reaction water formed during this process is removed in vacuo, 760 g (8.84 mol) of cyclopropanecarboxylic acid are then added, the mixture is subsequently heated to 200° C. in the course of 6 hours and under an atmosphere of inert gas, and any reaction water liberated is simultaneously distilled off. When the reaction is complete, the mixture is evaporated in vacuo to dryness, the residue is extracted using 3000 ml of boiling ethanol, the extract is filtered and cooled, and the crystalline precipitate which has formed is filtered off with suction and dried.

420 g (34% of theory) of 4-amino-3-cyclopropyl-1,2,4-(1H)-triazolin-5-one of melting point 181° C. are obtained.

The following are obtained in a corresponding manner:

Example III-2

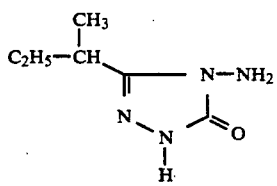

melting point 168° C.

Example III-3

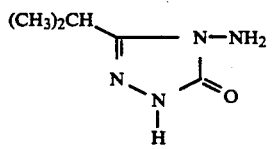

melting point 168° C.

Example III-4

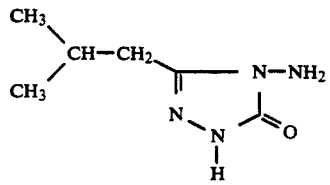

Example III-5

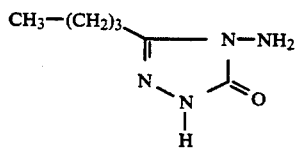

Example (III-6)

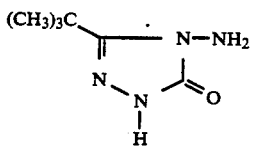

melting point 261° C.

Example III-7

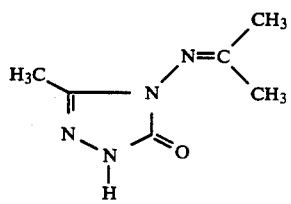

11.4 g (0.1 mol) of 4-amino-3-methyl-1H-1,2,4-triazolin-5-one (compare Europ. J.Med.Chem.: Chim. Ther. 18, 215-220 [1983]) and 0.1 g of p-toluenesulphonic acid in 100 ml (79.06 g; 1.36 mol) of acetone are stirred at 70° C. for 40 hours, and the mixture is then concentrated in vacuo. 15.4 g (100% of theory) of 4-isopropylideneimino-3-methyl-1H-1,2,4-triazolin-5-one of melting point 140°-144° C. are obtained.

Example VIII-1

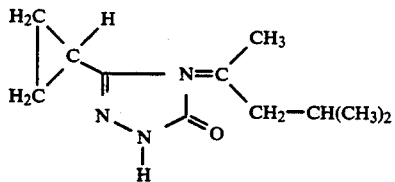

142 g (1.0 mol) of 4-amino-3-cyclopropyl-1,2,4-(1H)-triazolin-5-one in 1000 ml of methyl isobutyl ketone with the addition of 100 mg of p-toluenesulphonic acid are refluxed in a water separator until the liberation of further reaction water has ceased. For working up, the mixture is concentrated in vacuo, and the residue is crystallized by trituration with petroleum ether.

66 g (30% of theory) of 4-(4-methylpent-2-ylideneimino)-3-cyclopropyl-1,2,4-(1H)-triazolin-5-one of melting point 64° C. are obtained.

Example X-1

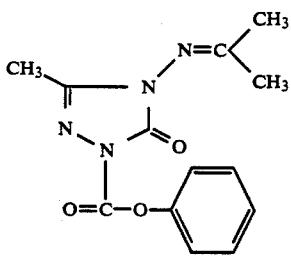

13.4 g (0.12 mol) of potassium-t-butylate are first added at room temperature to 15.4 g (0.1 mol) of 4-isopropylideneimino-3-methyl-1,2,4-(1H)-triazolin-5-one in 100 ml of absolute tetrahydrofuran, the mixture is stirred for one hour at room temperature, 15.5 g (0.1 mol) of phenyl chloroformate are then added and the mixture is stirred for a further 12 hours at 20° C.

For the working up the mixture is acidified with glacial acetic acid and concentrated in vacuo, the residue is taken up in chloroform and the solution is washed with water, dried over sodium sulphate, concentrated once again in vacuo and the residue recrystallized from acetone.

10 g (36.5% of theory) of 4-isopropylideneimino-3-methyl-1-phenoxycarbonyl-1,2,4-triazolin-5-one of a melting point of 162° C. are obtained.

Example X-2

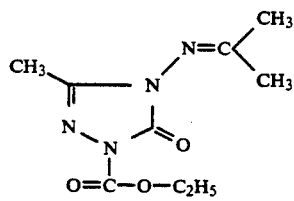

1.5 g (0.05 mol) of sodium hydride are added at 20° C. to 7.7 g (0.05 mol) of 4-isopropylideneimino-3-methyl-1,2,4-(1H)-triazolin-5-one in 50 ml of absolute tetrahydrofuran, the mixture is stirred for one hour at room temperature and then 5.4 g (0.05 mol) of ethyl chloroformate are added dropwise with stirring and when the addition has ended the mixture is stirred at 20° C. for a further 12 hours.

For the working up the mixture is acidified with glacial acetic acid and concentrated in vacuo, the residue is taken up in dichloromethane and the solution is washed with water, dried over sodium sulphate, concentrated once again in vacuo and the residue recrystallized from isopropanol.

5.0 g (44% of theory) of 1-ethoxycarbonyl-4-isopropylideneimino-3-methyl-1,2,4-triazolin-5-one of a melting point of 91° C. are obtained.

USE EXAMPLES

The compounds shown below were employed as the comparison substances in the following use examples:

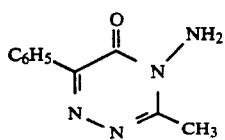

4-Amino-3-methyl-6-phenyl-1,2,4-triazin-5-one (known from DE-OS (German Published Specification) 2,364,474, Example I-22)

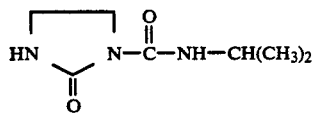

N-Isobutyl-2-oxoimidazolidine-1-carboxamide (known from R. Wegler "Chemie der Pflanzenschutz- und Schädlingsbekämpfungsmittel" Vol. 5, page 219 (1977)).

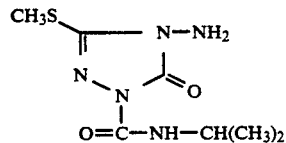

4-amino-1-(N-isopropylcarbamoyl)-3-methylthio(1H, 4H)-1,2,4-triazolin-5-one

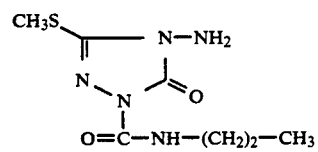

4-amino-1-(N-propylcarbamoyl)-3-methylthio-(1H, 4H)-1,2,4-triazolin-5-one

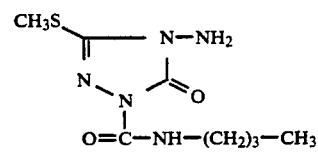

4-amino-1-(N-butylcarbamoyl)-3-methylthio-(1H, 4H)-1,2,4-triazolin-5-one and

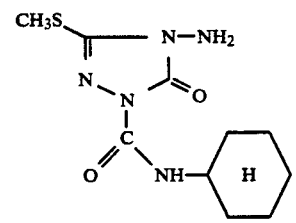

4-amino-1-(N-cyclohexylcarbamoyl)-3-methylthio-(1H, 4H)-1,2,4-triazolin-5-one;
all disclosed in JP 52/125,168.

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction.

In this test, for example, the compounds according to the preparation Examples 2, 14, 23, 32, 41, 45, 48 and 57 show a remarkedly better herbicidal activity against weeds and a remarkedly better selectivity in useful plants, such as, for example, sugar beets, than the comparison substance (B).

The compounds of Examples 164, 173, 181, 193, 197, 200 and 203 show similar good properties.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, for example, the compounds according to Examples 1, 2, 3, 14, 23, 32, 41, 45, 48, 57 and 78 show a distinctly better herbicidal action than the comparison substance (A) and (B), respectively in combating mono- and dicotelydon weeds.

The compounds of Examples 175, 181, 182, 193, 197, 199, 200, 201, 202 and 203 show similar good properties.

It will be understood that the specification and examples are illustrative but not limitative of the present invention and that other embodiments within the spirit and scope of the invention will suggest themselves to those skilled in the art.

We claim:
1. A hydrazone of the formula

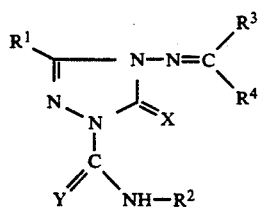

in which

R¹ represents hydrogen, methyl, ethyl, n- or i-propyl, i-, n-, s- or t-butyl, n- or i-pentyl, n- or i-hexyl; cyclopropyl, methoxymethyl, ethoxymethyl or propoxymethyl, R² represents hydrogen or represents methyl, ethyl, n- or i-propyl, n-, i-, s- or t-butyl, allyl, propargyl, in each case, straight-chain or branched pentyl, hexyl, heptyl, octyl, butenyl, pentenyl, hexenyl, butynyl, pentynyl, or hexynyl, each of which is optionally monosubstituted, disubstituted or trisubstituted by halogen; or additionally represents cyclopropyl, cyclopentyl, cyclohexyl, cyclohexenyl, cyclopropylmethyl, cyclopropylethyl, cyclohexylmethyl, cyclohexylethyl or cycloheptyl, which are in each case optionally monosubstituted, disubstituted or trisubstituted by identical or different substituents from the group consisting of fluorine, chlorine, methyl, ethyl and cyano; or represents benzyl, phenylethyl or phenyl, X represents oxygen or sulphur, Y represents oxygen or sulphur, and R³ and R⁴, independently of each other, each represents hydrogen, alkyl with 1 to 4 carbon atoms, phenyl or benzyl.

2. A compound according to claim 1, of the formula

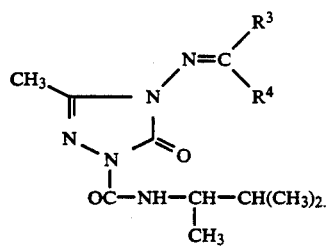

3. A hydrazone according to claim 1, in which

R¹ represents n-propyl, i-propyl, n-butyl, i-butyl s-butyl, t-butyl or cyclopropyl, and X and Y represent O.

4. A hydrazone according to claim 1, in which

R¹ represents i-propyl, s-butyl or cyclopropyl.

5. A compound according to claim 1, of the formula

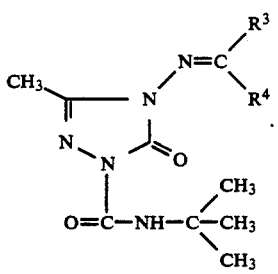

6. A compound according to claim 1, of the formula

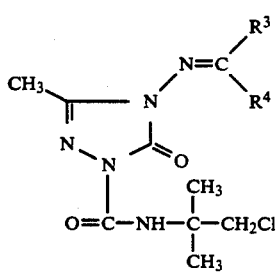

7. A compound according to claim 1, of the formula

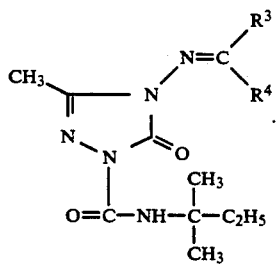

8. A compound according to claim 1, of the formula

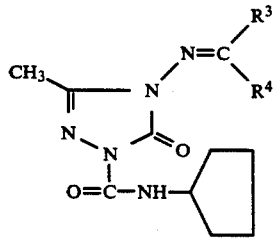

9. A compound according to claim 1, of the formula

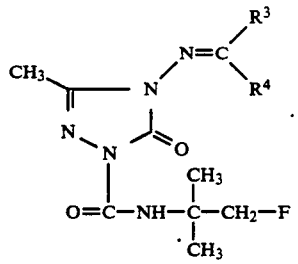
10. A compound according to claim 1, of the formula
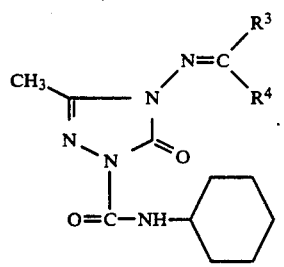
11. A compound according to claim 1, of the formula
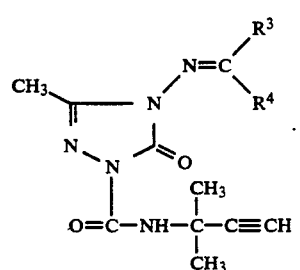
12. A compound according to claim 1, of the formula
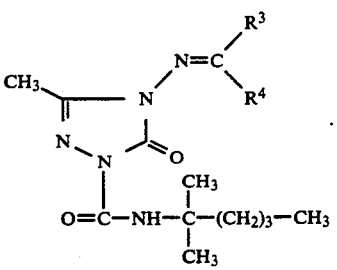
13. A compound according to claim 1, of the formula
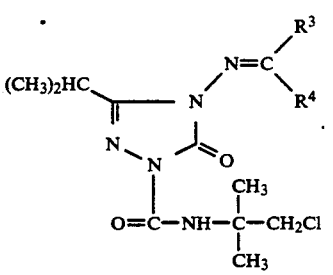
14. A compound according to claim 1, of the formula
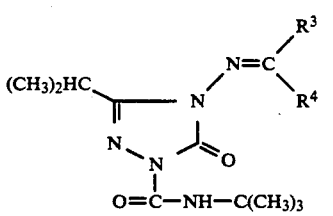
15. A compound according to claim 1, of the formula
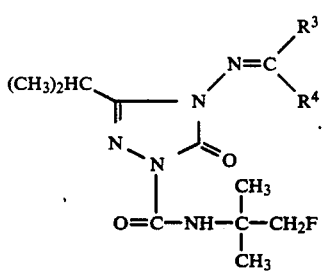
16. A compound according to claim 1, of the formula
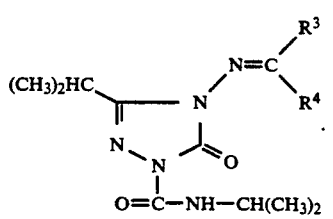
* * * * *

UNITED STATES PATENT AND TRADEMARK OFFICE
CERTIFICATE OF CORRECTION

PATENT NO. : 5,326,877

DATED : July 5, 1994

INVENTOR(S) : Lindig, et al.

It is certified that error appears in the above-identified patent and that said Letters Patent is hereby corrected as shown below:

Title Page   item: [60] Related U.S. Application Data:  Line 5 after " doned , " delete " which is " and substitute -- ; this is also --

Col. 73, line 55    Delete " 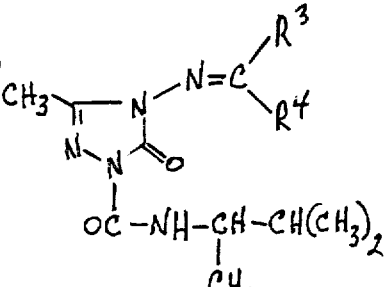 " and substitute

UNITED STATES PATENT AND TRADEMARK OFFICE
CERTIFICATE OF CORRECTION

PATENT NO. : 5,326,877

DATED : July 5, 1994

INVENTOR(S) : Lindig, et al.

Page 2 of 2

It is certified that error appears in the above-indentified patent and that said Letters Patent is hereby corrected as shown below:

and substitute --

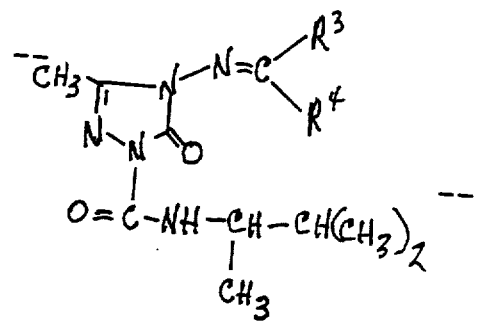

--

Signed and Sealed this

Third Day of January, 1995

Attest:

BRUCE LEHMAN

Attesting Officer

Commissioner of Patents and Trademarks